(12) United States Patent
Aasen et al.

(10) Patent No.: US 9,078,406 B2
(45) Date of Patent: Jul. 14, 2015

(54) SOYBEAN PLANT AND SEED CORRESPONDING TO TRANSGENIC EVENT MON87754 AND METHODS FOR DETECTION THEREOF

(75) Inventors: Eric Aasen, St. Louis, MO (US); David Chi, St. Louis, MO (US); Can Duong, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 1155 days.

(21) Appl. No.: 13/060,852

(22) PCT Filed: Jul. 15, 2009

(86) PCT No.: PCT/US2009/050619
§ 371 (c)(1),
(2), (4) Date: Jun. 22, 2011

(87) PCT Pub. No.: WO2010/024976
PCT Pub. Date: Mar. 4, 2010

(65) Prior Publication Data
US 2011/0252510 A1 Oct. 13, 2011

Related U.S. Application Data

(60) Provisional application No. 61/092,895, filed on Aug. 29, 2008, provisional application No. 61/094,803, filed on Sep. 5, 2008.

(51) Int. Cl.
| | |
|---|---|
| *C12N 15/82* | (2006.01) |
| *C12N 9/10* | (2006.01) |
| *C12Q 1/68* | (2006.01) |
| *C07H 21/04* | (2006.01) |
| *A23L 1/20* | (2006.01) |
| *A23L 1/305* | (2006.01) |
| *A01H 5/10* | (2006.01) |

(52) U.S. Cl.
CPC ............. *A01H 5/10* (2013.01); *C12N 15/8247* (2013.01); *A23L 1/2006* (2013.01); *A23L 1/3055* (2013.01); *C07H 21/04* (2013.01); *C12N 9/1025* (2013.01); *C12Q 1/6895* (2013.01)

(58) Field of Classification Search
None
See application file for complete search history.

(56) References Cited

U.S. PATENT DOCUMENTS

| | | | |
|---|---|---|---|
| 6,689,880 B2 | 2/2004 | Chen et al. | |
| 6,733,974 B1 | 5/2004 | Feazel | |
| 6,740,488 B2 | 5/2004 | Rangwala et al. | |
| 6,818,807 B2 | 11/2004 | Trolinder et al. | |
| 6,822,141 B2 | 11/2004 | Lardizabal et al. | |
| 6,825,400 B2 | 11/2004 | Behr et al. | |
| 6,893,826 B1 | 5/2005 | Hillyard et al. | |
| 6,900,014 B1 | 5/2005 | Weston et al. | |
| 7,135,617 B2 | 11/2006 | Lardizabal et al. | |

FOREIGN PATENT DOCUMENTS

| | | |
|---|---|---|
| WO | 00/01713 A2 | 1/2000 |
| WO | 2004011671 A2 | 2/2004 |
| WO | 2006108675 A2 | 10/2006 |

OTHER PUBLICATIONS

Genbank accession No. CR391917 (2006).*
Smith 2002 Genbank accession AC013737.*
Hohe et al 2003 Plant Cell Reports 21:1135-1142.*
Taverniers et al., "Event-Specific Plasmid Standards and Real-Time PCR Methods for Transgenic Bt11, Bt176, and GA21 Maize and Transgenic GT73 Canola", Journal of Agricultural and Food Chemistry, 2005, pp. 3041-3052, vol. 53.
Bennett et al., "Modification of Seed Oil Content in Soybean (*Glycine max*) by Expression of a *Mortierella ramanniana* Diacylglycerol Acyltransferase", http://abstracts.aspb.org/pb2004/public/P63/7307.html, Jul. 1, 2004, pp. 162-163.
Hildebrand et al., "Genomics of Soybean Oil Traits", Genetics and Genomics of Soybean, Jan. 1, 2008, pp. 185-209, Springer Science and Business Media, New York, NY, USA.
Lardizabal et al., "Expression of *Umbelopsis ramanniana* DGAT2A in Seed Increases Oil in Soybean", Plant Physiology, Sep. 2008, pp. 89-96, vol. 148, No. 1.
Settlage et al., "Relation Between Diacylglycerol Acyltransferase Activity and Oil Concentration in Soybean", Journal of the American Oil Chemists' Society, Jul. 1998, pp. 775-781, vol. 75, No. 7.

* cited by examiner

*Primary Examiner* — David T Fox
*Assistant Examiner* — Matthew Keogh
(74) *Attorney, Agent, or Firm* — Thompson Coburn LLP; J. Wendy Davis; Chunping Li

(57) ABSTRACT

The present invention provides the transgenic soybean event MON87754, and the cells, seeds, plant parts, and plants comprising DNA diagnostic for this transgenic soybean event. The event itself functions to increase the oil content of soybeans carrying the event in their genome relative to commodity versions of soy. The invention also provides compositions comprising nucleotide sequences that are diagnostic for said soybean event in a sample, methods for detecting the presence of said soybean event nucleotide sequences in a sample, probes and primers for use in detecting nucleotide sequences that are diagnostic for the presence of said soybean event in a sample, growing the seeds of such soybean event into soybean plants, and breeding to produce soybean plants comprising DNA diagnostic for the soybean event.

16 Claims, 2 Drawing Sheets

[F] SEQ ID NO: 6

[C] SEQ ID NO: 3                                    [D] SEQ ID NO: 4

[E] SEQ ID NO: 5

[A] SEQ ID NO:1                                    [B] SEQ ID NO:2

5' soybean   LB   P-Gm.Phas1   CR-Mr.Dgat2A.nno   T-Ps.RbcS2-E9   RB   3' soybean
MON87754                                                                MON87754
genome                                                                  genome

SOYBEAN PLANT AND SEED CORRESPONDING TO TRANSGENIC EVENT MON87754 AND METHODS FOR DETECTION THEREOF

CROSS REFERENCE TO RELATED APPLICATION

This application is a National Stage application of International Patent Application No. PCT/US2009/050619, filed Jul. 15, 2009 and incorporated herein by reference in its entirety, which claims the benefit of U.S. Provisional Application Ser. No. 61/092,895 filed on Aug. 29, 2008 and the benefit of U.S. Provisional Application Ser. No. 61/094,803 filed on Sep. 5, 2008.

INCORPORATION OF SEQUENCE LISTING

A sequence listing containing the file named 45_77_55949_C.txt, which is 19814 bytes (as measured in Microsoft Windows®) and created on Feb. 25, 2011, comprises 12 nucleotide sequences, and is herein incorporated by reference in its entirety.

FIELD OF THE INVENTION

The present invention relates to transgenic soybean event MON87754 and plants, plant parts and seeds thereof. The transgenic event exhibits elevated seed oil over commodity soy varieties. The invention also relates to methods for detecting the presence of said soybean transgenic event in a biological sample, and provides nucleotide sequences that are unique to the MON87754 event.

BACKGROUND OF THE INVENTION

This invention comprises the transgenic soybean (Glycine max) plant MON87754 with elevated seed oil over commodity soy varieties, the DNA construct of soybean plant MON87754, the detection of the transgene/genomic insertion region into soybeans creating the MON87754 event, the progeny thereof and the uses of the elevated oil provided by this invention.

Soybeans are an important crop worldwide and are a primary food source in many areas of the world. In the past, the methods and techniques of biotechnology have been applied to soybeans to improve certain agronomic traits, and the quality of the product. According to the current invention methods have been employed to enhance the soybean oil level produced in a plant which is elevated relative to commodity soy varieties.

In the process of developing transgenic soybeans it would be advantageous to be able to detect the presence of a specific transgene in the genomic DNA of a particular plant in order to determine whether progeny of a sexual cross contain the transgene/genomic DNA of interest. In addition, a method for detecting a particular plant with a specific transgenic insert would be helpful when complying with regulations requiring the pre-market approval and labeling of foods derived from the recombinant crop plants.

Triacylglycerol (TAG) is thought to be the most important storage unit of energy in plant cells. Diacylglycerol acyltransferase (DGAT) is an enzyme which is believed to regulate the chemical structure of TAG and to direct TAG synthesis. The reaction catalyzed by DGAT is at a critical branchpoint in glycerolipid biosynthesis. Enzymes at such branch points are considered prime candidates for sites of metabolic regulation. There are several enzymes which are common to the synthesis of diacylglycerol, TAG and membrane lipids, however the DGAT reaction is specific for oil synthesis.

In plants, TAG is the primary component of vegetable oil that is used by the seed as a stored form of energy to be used during seed germination. Higher plants appear to synthesize oils via a common metabolic pathway. Fatty acids are made in plastids from acetyl-CoA through a series of reactions catalyzed by enzymes known collectively as Fatty Acid Synthase (FAS). The fatty acids produced in plastids are exported to the cytosolic compartment of the cell, and are esterified to coenzyme A. These acyl-CoAs are the substrates for glycerolipid synthesis in the endoplasmic reticulum (ER). Glycerolipid synthesis itself is a series of reactions leading first to phosphatidic acid (PA) and Diacylglycerol (DAG). Either of these metabolic intermediates may be directed to membrane phospholipids such as phosphatidylglycerol (PG) phosphatidylethanolamine (PE) or phosphatidylcholine (PC) or they may be directed on to form neutral triacylglycerol (TAG).

Diacylglycerol (DAG) is synthesized from glycerol-3-phosphate and fatty acyl-CoAs in two steps catalyzed sequentially by glycerol-3-phosphate acyltransferase (G3PAT), and lysophosphatidic acid acyltransferase (LPAAT) to make PA, and then an additional hydrolytic step catalyzed by phosphatidic acid phosphatase (PAP) to make DAG. In most cells, DAG is used to make membrane phospholipids, the first step being the synthesis of PC catalyzed by CTP-phosphocholine cytidylyltransferase. In cells producing storage oils, DAG is acylated with a third fatty acid in a reaction catalyzed by diacylglycerol acyltransferase (DGAT). Collectively, the reactions make up part of what is commonly referred to as the Kennedy Pathway.

TAGs present in plants and animals are important molecules as energy reserve. In oilseed crops, TAG plays a major role as storage lipids and utilized as plants oil. Crude soybean oil, which is traded at international grain market as 'soybean oil', is composed of 95-97% triacylglycerols (TAGs), and refined soybean oil for edible use is composed of >99% TAGs (Perkins, 1995); therefore any increase in triacylglycerols leads to an increase in soybean oil content.

Soybeans are the largest source of vegetable oil worldwide (USDA, 2007). The world demand for vegetable oil grows at an accelerating rate driven by the rapid economical expansion in the emerging markets such as China and India. In recent years energy prices have risen to historical record level and will most likely stay high for the foreseeable future. This energy price surge has further stimulated demand for alternative energy sources including biodiesel, which can be produced from soybean oil. Thus with soybean oil becoming more valuable, traits that increase total soybean oil content will improve the total value of this crop.

Controlled expression of the DGAT gene in a transgenic plant to produce a seed with a higher ratio of oil to seed meal would be useful to obtain a desired oil at a lower cost. This would be typical of a high value oil product. Or such an oilseed might constitute a superior feed for animals. In some instances having an oilseed with a lower ratio of oil to seed meal would be useful to lower caloric content. In other uses, edible plant oils with a higher percentage of unsaturated fatty acids are desired for cardiovascular health reasons. And alternatively, temperate substitutes for high saturate tropical oils such as palm, coconut or cocoa would also find uses in a variety of industrial and food applications.

The expression of foreign genes in plants is known to be influenced by their chromosomal position, perhaps due to chromatin structure (e.g., heterochromatin) or the proximity of transcriptional regulation elements (e.g., enhancers) close to the integration site Weising et al. (1988 Ann. Rev. Genet 22:421-477). For this reason, it is often necessary to screen a large number of events in order to identify an event characterized by optimal expression of an introduced gene of interest. For example, it has been observed in plants and in other organisms that there may be wide variation in the levels of expression of an introduced gene among events. There may also be differences in spatial or temporal patterns of expression, for example, differences in the relative expression of a transgene in various plant tissues, that may not correspond to the patterns expected from transcriptional regulatory elements present in the introduced gene construct. For this reason, it is common to produce several hundreds to several thousands different events and screen the events for a single event that has the desired transgene expression levels and patterns for commercial purposes. An event that has the desired levels or patterns of transgene expression is useful for introgressing the transgene into other genetic backgrounds by sexual outcrossing using conventional breeding methods. Progeny of such crosses maintain the transgene expression characteristics of the original transformant. This strategy is used to ensure reliable gene expression in a number of varieties that are suitably adapted to specific local growing conditions.

It is possible to detect the presence of a transgene by any well known nucleic acid detection method such as the polymerase chain reaction (PCR) or DNA hybridization using nucleic acid probes. These detection methods generally focus on frequently used genetic elements, such as promoters, terminators, marker genes, etc. As a result, such methods may not be useful for discriminating between different events, particularly those produced using the same DNA construct unless the sequence of chromosomal DNA adjacent to the inserted DNA ("flanking DNA") is known. An event-specific PCR assay is discussed, for example, by Taverniers et al. (J. Agric. Food Chem., 53: 3041-3052, 2005) in which an event-specific tracing system for transgenic maize lines Bt11, Bt176, and GA21 and for canola event GT73 is demonstrated. In this study, event-specific primers and probes were designed based upon the sequences of the genome/transgene junctions for each event. Transgenic plant event specific DNA detection methods have also been described in U.S. Pat. Nos. 6,893,826; 6,825,400; 6,740,488; 6,733,974; 6,689,880; 6,900,014 and 6,818,807.

SUMMARY OF THE INVENTION

The present invention is related to the transgenic soybean plant designated MON87754 and progeny that are indistinguishable from soybean event MON87754 (to the extent that such progeny also contain at least one allele that corresponds to the inserted transgenic DNA) thereof having seed deposited with American Type Culture Collection (ATCC) with Accession No. PTA-9385. Another aspect of the invention is the progeny plants, or seeds, or regenerable parts of the plants and seeds of the soybean event MON87754. The invention also includes plant parts of the soybean event MON87754 that include, but are not limited to pollen, ovule, flowers, shoots, roots, stems, leaves, pods, seeds and meristematic tissues. Novel genetic compositions contained in the genome of MON87754 and products from MON87754 such as oil, meal, flour, food products, protein supplements and biomasses remaining in a field from which soybean plants corresponding to MON87754 have been harvested are aspects of this invention.

The invention provides a soybean plant with elevated seed oil over commodity soy varieties and that has all of the physiological and morphological characteristics of the soybean event MON87754.

According to one aspect of the invention, compositions and methods are provided for detecting the presence of the transgene/genomic insertion region from a novel soybean plant designated MON87754. DNA sequences are provided that comprise at least one junction sequence of MON87754 selected from the group consisting of SEQ ID NO: 1 ([A] corresponding to positions 942 through 961 of SEQ ID NO: 6 [F], FIG. 2) and SEQ ID NO: 2 ([B] corresponding to positions 3978 through 3997 of SEQ ID NO: 6 [F], FIG. 2) and compliments thereof; wherein a junction sequence is a nucleotide sequence that spans the point at which heterologous DNA inserted into the genome is linked to the soybean cell genomic DNA and detection of this sequence in a biological sample containing soybean DNA is diagnostic for the presence of the soy event MON87754 DNA in said sample (FIG. 2). Such junction sequences contain at least SEQ ID NO: 1 and/or SEQ ID NO: 2 and/or the compliments thereof. A soybean event MON87754 and soybean seed comprising these DNA molecules is an aspect of this invention.

DNA sequences that comprise novel transgene/genomic insertion region, SEQ ID NO: 3 [C], SEQ ID NO: 4 [D] and SEQ ID NO: 5 [E] or SEQ ID NO: 1 [A], SEQ ID NO: 2 [B] and SEQ ID NO: 5 [E] (see FIG. 2) from soybean event MON87754 are aspects of this invention. The soybean plant and seed comprising these molecules are also aspects of this invention.

According to another aspect of the invention, two DNA molecules are provided for use in a DNA detection method, wherein the first DNA molecule comprises at least 11 or more contiguous polynucleotides of any portion of the transgene region of the DNA molecule of SEQ ID NO: 3 or SEQ ID NO: 5 and a DNA molecule of similar length of any portion of a 5' flanking soybean genomic DNA region of SEQ ID NO: 3, where these DNA molecules when used together are useful as DNA primers in a DNA amplification method that produces an amplicon. The amplicon produced using these DNA primers in the DNA amplification method is diagnostic for soybean event MON87754 when the amplicon contains SEQ ID NO: 1. Any amplicon produced by DNA primers homologous or complementary to any portion of SEQ ID NO: 3 and SEQ ID NO: 5, and any amplicon that comprises SEQ ID NO: 1 is an aspect of the invention.

According to another aspect of the invention, two DNA molecules are provided for use in a DNA detection method, wherein the first DNA molecule comprises at least 11 or more contiguous polynucleotides of any portion of the transgene region of the DNA molecule of SEQ ID NO: 4 or SEQ ID NO: 5 and a DNA molecule of similar length of any portion of a 3' flanking soybean genomic DNA of SEQ ID NO: 4, where these DNA molecules are useful as DNA primers in a DNA amplification method. The amplicon produced using these DNA primers in the DNA amplification method is diagnostic for soybean event MON87754 when the amplicon contains SEQ ID NO: 2. Any amplicons produced by DNA primers homologous or complementary to any portion of SEQ ID NO: 4 and SEQ ID NO: 5, and any amplicon that comprises SEQ ID NO: 2 is an aspect of the invention.

According to another aspect of the invention, methods of detecting the presence of DNA corresponding to the soybean event MON87754 in a sample are provided. Such methods comprise: (a) contacting the sample comprising DNA with a primer set that, when used in a nucleic acid amplification reaction with genomic DNA from soybean event MON87754, produces an amplicon that is diagnostic for soybean event MON87754; (b) performing a nucleic acid amplification reaction, thereby producing the amplicon; and (c) detecting the amplicon wherein said amplicon comprises SEQ ID NO: 1 and/or SEQ ID NO: 2.

Another aspect of the invention is a soybean plant, or seed, or product derived from the plant or seed of MON87754 wherein the genomic DNA comprises a DNA molecule consisting essentially of the nucleotide sequence of SEQ ID NO: 3 from about positions 1 to 950, the nucleotide sequence of SEQ ID NO: 5 from about positions 1 to 3036 and the nucleotide sequence of SEQ ID NO: 4 from about positions 144 to 1244 (the contig of which is presented as SEQ ID NO: 6), and complements thereof. A soybean plant, or seed, or product derived from the plant or seed MON87754, in which the genomic DNA when isolated from the soybean plant, or seed, or product comprises a DNA molecule incorporating SEQ ID NO: 1 and/or SEQ ID NO: 2, and complements thereof.

A further aspect of the invention is a soybean plant, or seed, or product derived from the plant or seed of MON87754 wherein the genomic DNA comprises a DNA molecule consisting essentially of the nucleotide sequence of SEQ ID NO: 6 from about positions 1 to 5087 and complements thereof. A soybean plant, or seed, or product derived from the plant or seed MON87754, in which the genomic DNA when isolated from the soybean plant, or seed, or product comprises a DNA molecule incorporating SEQ ID NO: 1 and/or SEQ ID NO: 2, and complements thereof.

Another aspect of the invention is a soybean plant, or seed, or product derived from the plant or seed of MON87754, in which the genomic DNA when isolated from the soybean plant, or seed, or product produces an amplicon in a DNA amplification method, wherein said amplicon comprises SEQ ID NO: 1 and/or SEQ ID NO: 2.

According to another aspect of the invention, methods of detecting the presence of a DNA corresponding to the MON87754 event in a sample, such methods comprising: (a) contacting the sample comprising DNA with a probe that hybridizes under stringent hybridization conditions with genomic DNA from soybean event MON87754 and does not hybridize under the stringent hybridization conditions with a control soybean plant; (b) subjecting the sample and probe to stringent hybridization conditions; and (c) detecting hybridization of the probe to the soybean event MON87754 DNA wherein said probe is selected from the group consisting of SEQ ID NO:1 and/or SEQ ID NO:2.

Another aspect of the invention is a method of determining zygosity of the progeny of soybean event MON87754, the method comprising (a) contacting the sample comprising soybean DNA with the primer set SQ20209 (SEQ ID NO: 8), SQ20331 (SEQ ID NO: 9), SQ20332 (SEQ ID NO: 11), and the probe set 6FAM™-labeled PB10090 (SEQ ID NO: 10) and VIC™-labeled PB10091 (SEQ ID NO: 12) that when used in a nucleic-acid amplification reaction with genomic DNA from soybean event MON87754, produces a first amplicon, releasing a fluorescent signal from the combination of primers SQ20209 (SEQ ID NO: 8) and SQ20331 (SEQ ID NO: 9) and a 6FAM™-labeled primer/probe, PB10090 (SEQ ID NO: 10) that is diagnostic for soybean event MON87754 (b) performing a nucleic acid amplification reaction, thereby producing the first amplicon; and (c) detecting said first amplicon; and (d) contacting the sample comprising soybean DNA with the primer set, SQ20331 and SQ20332 and a VIC™-labeled probe, PB10091 that when used in a nucleic-acid amplification reaction with genomic DNA from soybean plants produces a second amplicon, releasing a fluorescent signal that is diagnostic of the wild-type soybean genomic DNA homologous to the soybean genomic region of a transgene insertion identified as soybean event MON87754; (e) performing a nucleic acid amplification reaction, thereby producing the second amplicon and (f) detecting said second amplicon; and (g) comparing the first and second amplicons in a sample, wherein the presence of both amplicons indicates the sample is heterozygous for the transgene insertion.

Another aspect of the invention is a method of determining zygosity of the progeny of soybean event MON87754, the method comprising (a) contacting the sample comprising soybean DNA with the primer set SQ20209 (SEQ ID NO: 8), SQ20331 (SEQ ID NO: 9), and SQ20332 (SEQ ID NO: 11), that when used in a nucleic-acid amplification reaction with genomic DNA from soybean event MON87754, produces a first amplicon from the combination of primers SQ20209 (SEQ ID NO: 8) and SQ20331 (SEQ ID NO: 9) that is diagnostic for soybean event MON87754 (b) performing a nucleic acid amplification reaction, thereby producing the first amplicon; and (c) detecting said first amplicon; and (d) contacting the sample comprising soybean DNA with the primer set, SQ20331 (SEQ ID NO: 9) and SQ20332 (SEQ ID NO: 11) that when used in a nucleic-acid amplification reaction with genomic DNA from soybean plants produces a second amplicon from the combination of primers SQ20331 and SQ20332 that is diagnostic of the wild-type soybean genomic DNA homologous to the soybean genomic region of a transgene insertion identified as soybean event MON87754; (e) performing a nucleic acid amplification reaction, thereby producing the second amplicon and (f) detecting said second amplicon; and (g) comparing the first and second amplicons in a sample, wherein the presence of both amplicons indicates the sample is heterozygous for the transgene insertion.

Kits for the detection of soybean event MON87754 are provided which use primers designed from SEQ ID NO: 3, SEQ ID NO: 4 and SEQ ID NO: 5. An amplicon produced using said kit is diagnostic for MON87754 when the amplicon (1) contains either nucleotide sequences set forth as SEQ ID NO: 1 or SEQ ID NO: 2 or (2) contains both SEQ ID NO: 1 and SEQ ID NO: 2.

Another aspect of the invention is a soybean plant, or seed, or seed progeny, or product derived from the plant or seed of MON87754. Seed for sale for planting or for making commodity products is an aspect of the invention. Such commodity products include, but are not limited to, whole or processed soy seeds, animal feed, aquafeed for use in aquaculture, vegetable oil, meal, flour, nontoxic plastics, printing inks, lubricants, waxes, hydraulic fluids, electric transformer fluids, solvents, cosmetics, hair care products, soymilk, soy nut butter, natto, tempeh, soy protein concentrate, soy protein isolates, texturized soy protein concentrate, hydrolyzed soy protein, whipped topping, cooking oil, salad oil, shortening, lecithin, edible whole soybeans (raw, roasted, or as edamamé), soymilk, soy yogurt, soy cheese, tofu, yuba and biodiesel.

The foregoing and other aspects of the invention will become more apparent from the following detailed description.

BRIEF DESCRIPTION OF THE DRAWINGS

FIG. 2. Organization of the transgenic insert in the genome of soybean event MON87754; [A] corresponds to the relative position of SEQ ID NO: 1 which forms the junction between SEQ ID NO: 3 and SEQ ID NO: 5; [B] corresponds to the relative position of SEQ ID NO: 2 which forms the junction between SEQ ID NO: 4 and SEQ ID NO: 5; [C] corresponds to the relative position of SEQ ID NO: 3, the soybean genome sequence flanking the arbitrarily assigned/designated 5' end of the expression cassette integrated into the genome in event MON87754; [D] corresponds to the relative position of SEQ ID NO: 4, the soybean genome sequence flanking the arbitrarily assigned/designated 3' end of the expression cassette integrated into the genome in event MON87754; [E] represents the various elements comprising SEQ ID NO: 5 and is the sequence of the expression cassette inserted into the genome of the event MON87754; and [F] represents the contiguous sequence comprising, as represented in the figure from left to right, SEQ ID NO:3, SEQ ID NO:5 and SEQ ID NO:4, in which SEQ ID NO:1 and SEQ ID NO:2 are incorporated as set forth above, as these sequences are present in the genome in event MON87754.

BRIEF DESCRIPTION OF THE SEQUENCES

Figure 1:
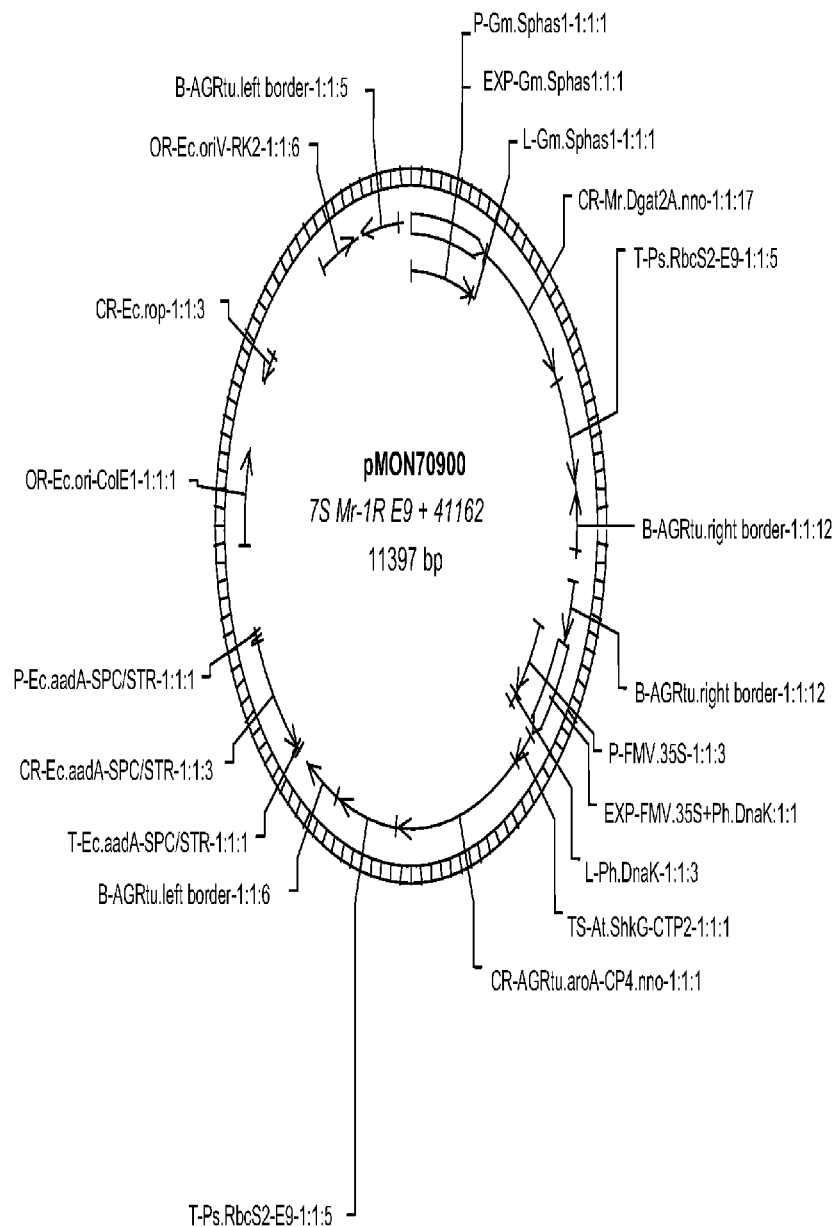
FIG. 1. Map of binary transformation vector, pMON70900 that was used to generate soybean plant MON87754.

SEQ ID NO: 1—A 20 nucleotide sequence representing the left border junction between the soybean genomic DNA and the integrated expression cassette. This sequence corresponds to positions 942 to 961 of SEQ ID NO: 6. In addition, SEQ ID NO: 1 ([A] of FIG. 2) is a nucleotide sequence corresponding to positions 942 through 961 of SEQ ID NO: 3 ([C], see FIG. 2). Positions 11 through 20 of SEQ ID NO: 1 also correspond to the integrated left border of the diacylglycerol acyltransferase expression cassette corresponding to positions 1 through 10 of SEQ ID NO: 5 ([E], see FIG. 2).

SEQ ID NO: 2—A 20 nucleotide sequence representing the right border junction between the integrated expression cassette and the soybean genomic DNA. This sequence corresponds to positions 3978 to 3997 of SEQ ID NO: 6. In addition, the first 10 nucleotides of SEQ ID NO: 2 ([B], see FIG. 2) correspond to positions 3027 through 3036 of SEQ ID NO: 5 ([E], see FIG. 2) and positions 11 through 20 of SEQ ID NO: 2 correspond to the 3' flanking sequence corresponding to positions 144 through 153 of SEQ ID NO: 4 ([D], see FIG. 2).

SEQ ID NO: 3—The 5' sequence flanking the inserted DNA of MON87754 up to and including a region of T-DNA insertion.

SEQ ID NO: 4—The 3' sequence flanking the inserted DNA of MON87754 up to and including a region of T-DNA insertion.

SEQ ID NO: 5—The sequence of the integrated diacylglycerol acyltransferase expression cassette, including right and left border sequence after integration.

SEQ ID NO: 6—A 5087 bp nucleotide sequence representing the contig of the 5' sequence flanking the inserted DNA of MON87754 (SEQ ID NO: 3), the sequence of the integrated expression cassette (SEQ ID NO: 5) and the 3' sequence flanking the inserted DNA of MON87754 (SEQ ID NO: 4).

SEQ ID NO: 7—The diacylglycerol acyltransferase expression cassette of pMON70900.

SEQ ID NO: 8—Primer SQ20209 used to identify MON87754 events as well as the zygosity of MON87754 events. Primer SQ20209 is complimentary to the 3' region flanking the inserted diacylglycerol acyltransferase cassette close to the right T-DNA insertion border corresponding to positions 4000 to 4026 of SEQ ID NO: 6. A PCR amplicon using the combination of primers SQ20331 and SQ20209 is positive for the presence of the event MON87754.

SEQ ID NO: 9—Primer SQ20331 used to identify MON87754 events. Primer SQ20331 corresponds to the 3' region of the inserted diacylglycerol acyltransferase cassette, close to the right T-DNA insertion border corresponding to positions 3954 to 3974 of SEQ ID NO: 6. A PCR amplicon using the combination of primers SQ20331 and SQ20209 is positive for the presence of the event MON87754.

SEQ ID NO: 10—Probe PB10090 used to identify MON87754 events. This probe is a 6FAM™-labeled synthetic oligonucleotide whose sequence corresponds to positions 3979 to 3997 of SEQ ID NO: 6. Release of a fluorescent signal in an amplification reaction using primers SQ20331 and SQ20209 in combination with 6FAM™-labeled probe PB10090 is diagnostic of event MON87754.

SEQ ID NO: 11—Primer SQ20332 used to determine zygosity of MON87754 events. Primer SQ20332 corresponds to the 3' region flanking the inserted expression cassette, close to the left T-DNA corresponding to positions 917 to 963 of SEQ ID NO: 6. Detection of a PCR amplicon using VIC™-labeled Probe PB10091 and primers SQ20331 and SQ20209 is positive for presence of wild type in a zygosity assay.

SEQ ID NO: 12—Probe PB10091 used to determine zygosity of MON87754 events. This probe is a VIC™-labeled synthetic oligonucloetide whose sequence corresponds to a region of the wild-type genomic DNA, immediately following the region of homology to primer SQ20332 at the point of insertion of the expression cassette for event MON87754. A PCR amplicon produced using primers SQ20209 and SQ20332 causes the release of a fluorescent signal using probe PB10091 which is positive for the presence of the wild-type allele in a zygosity assay for event MON87754.

DETAILED DESCRIPTION OF THE PREFERRED EMBODIMENTS

The following definitions and methods are provided to better define the present invention and to guide those of ordinary skill in the art in the practice of the present invention. Unless otherwise noted, terms are to be understood according to conventional usage by those of ordinary skill in the relevant art. Definitions of common terms in molecular biology may also be found in Rieger et al., *Glossary of Genetics: Classical and Molecular*, 5th edition, Springer-Verlag: New York, 1991; and Lewin, Genes V, Oxford University Press: New York, 1994.

As used herein, the term "soybean" means Glycine max and includes all plant varieties that can be bred with soybean, including wild soybean species as well as those plants belonging to Glycine soja that permit breeding between species.

As used herein, the term "comprising" means "including but not limited to".

"Glyphosate" refers to N-phosphonomethylglycine and its salts. N-phosphonomethylglycine is a well-known herbicide that has activity on a broad spectrum of plant species.

"Diacylglycerol acyltransferase" or "DGAT" is an enzyme that regulates the structure and directs the synthesis of triacylglycerol, a molecule which is important for energy storage in the cell. MrDGAT2A is one of the known isoforms of DGAT that is isolated from *Mortierella ramanniana*, a filamentous fungus which stores up to 80% of its dry weight as TAG. For plant expression, the MrDGAT2A gene was resynthesized to provide appropriate plant codon usage (MrDGAT2A.nno). Recently there have been changes to the internationally-accepted nomenclature for *Mortierella ramanniana*. This organism is now classified as *Umbellopsis ramanniana*. These two names are used interchangeably herein.

A "commodity product" refers to any product which is comprised of material derived from soybean or soybean oil and is sold to consumers. Processed soybeans are the largest source of protein feed and vegetable oil in the world. The soybean plant MON87754 can be used to manufacture commodities typically acquired from soy. Soybeans of MON87754 can be processed into meal, flour, or oil as well as be used as a protein or oil source in animal feeds for both terrestrial and aquatic animals. Soybeans and soybean oils from MON87754 can be used in the manufacture of many different products, not limited to, nontoxic plastics, printing inks, lubricants, waxes, hydraulic fluids, electric transformer fluids, solvents, cosmetics, and hair care products. Soybeans and oils of MON87754 can be suitable for use in a variety of soyfoods made from whole soybeans, such as soymilk, soy nut butter, natto, and tempeh, and soyfoods made from processed soybeans and soybean oil, including soybean meal, soy flour, soy protein concentrate, soy protein isolates, texturized soy protein concentrate, hydrolyzed soy protein, whipped topping, cooking oil, salad oil, shortening, and lecithin Whole soybeans are also edible, and are typically sold to consumers raw, roasted, or as edamamé. Soymilk, which is typically produced by soaking and grinding whole soybeans, may be consumed without other processing, spray-dried, or processed to form soy yogurt, soy cheese, tofu, or yuba.

Oils of MON87754 can be used to make biodiesel. The use of biodiesel in conventional diesel engines results in substantial reductions of pollutants such as sulfates, carbon monoxide, and particulates compared to petroleum diesel fuel, and use in school buses can greatly reduce exposure to toxic diesel exhaust. Biodiesel is typically obtained by extracting, filtering and refining soybean oil to remove free fats and phospholipids, and then transesterifying the oil with methanol to form methyl esters of the fatty acids (see for example U.S. Pat. No. 5,891,203). The resultant soy methyl esters are commonly referred to as "biodiesel." The oil derived from MON87754 may also be used as a diesel fuel without the formation of methyl esters, such as, for example, by mixing acetals with the oil (see for example U.S. Pat. No. 6,013,114). The seeds of MON87754 used to make said oils can be identified by the methods of the present invention. It is expected that purified oil from MON87754 event seeds or mixtures of seeds some or all of which are MON87754 will have relatively no DNA available for testing. However, the seeds from which the oils are extracted can be characterized with the method of the present invention to identify the presence of the MON87754 event within the population of seeds used to make said oils. Also, plant waste from the process used to make said oils can be used in the methods of the present invention to identify the presence of MON87754 events within a mixture of seeds processed to make said oils. Likewise, plant debris left after making a commodity product, or left behind following harvest of the soybean seed, can be characterized by the methods of the present invention to identify MON87754 events within the raw materials used to make said commodity products.

A transgenic "event" is produced by transformation of plant cells with heterologous DNA, i.e., a nucleic acid construct that includes a transgene of interest, regeneration of a population of plants resulting from the insertion of the transgene into the genome of the plant, and selection of a particular plant characterized by insertion into a particular genome location. The term "event" refers to the original transformant and progeny of the transformant that include the heterologous DNA. The term "event" also refers to progeny produced by a sexual outcross between the transformant and another variety that include the heterologous DNA. Even after repeated backcrossing to a recurrent parent, the inserted DNA and flanking DNA from the transformed parent is present in the progeny of the cross at the same chromosomal location. The term "event" also refers to DNA from the original transformant comprising the inserted DNA and flanking genomic sequence immediately adjacent to the inserted DNA that would be expected to be transferred to a progeny that receives inserted DNA including the transgene of interest as the result of a sexual cross of one parental line that includes the inserted DNA (e.g., the original transformant and progeny resulting from selfing) and a parental line that does not contain the inserted DNA. The present invention relates to the event MON87754 DNA, plant cells, tissues, seeds and processed products derived from MON87754.

It is also to be understood that two different transgenic plants can also be mated to produce offspring that contain two independently segregating added, exogenous genes. Selfing of appropriate progeny can produce plants that are homozygous for both added, exogenous genes. Back-crossing to a parental plant and out-crossing with a non-transgenic plant are also contemplated, as is vegetative propagation. Descriptions of other breeding methods that are commonly used for different traits and crops can be found in one of several references, e.g., Fehr, in *Breeding Methods for Cultivar Development*, Wilcox J. ed., American Society of Agronomy, Madison Wis. (1987).

As used herein when referring to an "isolated DNA molecule", it is intended that the DNA molecule be one that is present, alone or in combination with other compositions, but not within its natural environment. For example, a coding sequence, intron sequence, untranslated leader sequence, promoter sequence, transcriptional termination sequence, and the like, that are naturally found within the DNA of a soybean genome are not considered to be isolated from the soybean genome so long as they are within the soybean genome. However, each of these components, and subparts of these components, would be "isolated" within the scope of this disclosure so long as the structures and components are not within the soybean genome. Similarly, a nucleotide sequence encoding an *Umbellopsis ramanniana* diacylglycerol acyltransferase protein or a *Mortierella ramanniana* diacylglycerol acyltransferase protein would be an isolated nucleotide sequence so long as the nucleotide sequence was not within the DNA of the organism (*U. ramanniana* or *M. ramanniana*) from which the structure was first observed. An artificial nucleotide sequence encoding the same amino acid sequence or a substantially identical amino acid sequence that the native *U. ramanniana* nucleotide sequence encodes would be considered to be isolated for the purposes of this disclosure. For the purposes of this disclosure, any transgenic nucleotide sequence, i.e., the nucleotide sequence of the DNA inserted into the genome of the cells of the soybean plant event MON87754 would be considered to be an isolated nucleotide sequence whether it is present within the plasmid used to transform soybean cells from which the MON87754 event arose, within the genome of the event MON87754, present in detectable amounts in tissues, progeny, biological samples or commodity products derived from the event MON87754. The nucleotide sequence or any fragment derived therefrom would therefore be considered to be isolated or isolatable if the DNA molecule can be extracted from cells, or tissues, or homogenate from a plant or seed or plant organ; or can be produced as an amplicon from extracted DNA or RNA from cells, or tissues, or homogenate from a plant or seed or plant organ, any of which is derived from such materials derived from the event MON87754. For that matter, the junction sequences as set forth at SEQ ID NO:1 and SEQ ID NO:2, and nucleotide sequences derived from event MON87754 that also contain these junction sequences are considered to be isolated or isolatable, whether these sequences are present within the genome of the cells of event MON87754 or present in detectable amounts in tissues, progeny, biological samples or commodity products derived from the event MON87754.

A "probe" is an isolated nucleic acid to which is attached a conventional detectable label or reporter molecule, e.g., a radioactive isotope, ligand, chemiluminescent agent, or enzyme. Such a probe is complementary to a strand of a target nucleic acid, in the case of the present invention, to a strand of genomic DNA from soybean event MON87754 whether from a soybean plant or from a sample that includes DNA from the event. Probes according to the present invention include not only deoxyribonucleic or ribonucleic acids but also polyamides and other probe materials that bind specifically to a target DNA sequence and such binding can be used to detect the presence of that target DNA sequence.

"Primers" are isolated nucleic acids that are annealed to a complementary target DNA strand by nucleic acid hybridization to form a hybrid between the primer and the target DNA strand, and then extended along the target DNA strand by a polymerase, e.g., a DNA polymerase. Primer pairs of the present invention refer to their use for amplification of a target nucleic acid sequence, e.g., by the polymerase chain reaction (PCR) or other conventional nucleic-acid amplification methods.

Probes and primers are generally 11 nucleotides or more in length, preferably 18 nucleotides or more, more preferably 24 nucleotides or more, and most preferably 30 nucleotides or more. Such probes and primers hybridize specifically to a target sequence under high stringency hybridization conditions. Preferably, probes and primers according to the present invention have complete sequence similarity with the target sequence, although probes differing from the target sequence and that retain the ability to hybridize to target sequences may be designed by conventional methods.

Methods for preparing and using probes and primers are described, for example, in *Molecular Cloning: A Laboratory Manual,* 2nd ed., vol. 1-3, ed. Sambrook et al., Cold Spring Harbor Laboratory Press, Cold Spring Harbor, N.Y., 1989 (hereinafter, "Sambrook et al., 1989"); *Current Protocols in Molecular Biology*, ed. Ausubel et al., Greene Publishing and Wiley-Interscience, New York, 1992 (with periodic updates) (hereinafter, "Ausubel et al., 1992"); and Innis et al., *PCR Protocols: A Guide to Methods and Applications*, Academic Press: San Diego, 1990. PCR-primer pairs can be derived from a known sequence, for example, by using computer programs intended for that purpose such as Primer (Version 0.5., © 1991, Whitehead Institute for Biomedical Research, Cambridge, Mass.).

Primers and probes based on the flanking DNA and insert sequences disclosed herein can be used to confirm (and, if necessary, to correct) the disclosed sequences by conventional methods, e.g., by re-cloning and sequencing such sequences.

The nucleic acid probes and primers of the present invention hybridize under stringent conditions to a target DNA sequence. Any conventional nucleic acid hybridization or amplification method can be used to identify the presence of DNA from a transgenic event in a sample. Nucleic acid molecules or fragments thereof are capable of specifically hybridizing to other nucleic acid molecules under certain circumstances. As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., 1989, and by Haymes et al., In: *Nucleic Acid Hybridization, A Practical Approach*, IRL Press, Washington, D.C. (1985). Departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed.

As used herein, a substantially homologous sequence is a nucleic acid sequence that will specifically hybridize to the complement of the nucleic acid sequence to which it is being compared under high stringency conditions. Appropriate stringency conditions which promote DNA hybridization, for example, 6.0× sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. In a preferred embodiment, a nucleic acid of the present invention will specifically hybridize to one or more of the nucleic acid molecules set forth in SEQ ID NO: 1 and 2 or complements thereof or fragments of either under moderately stringent conditions, for example at about 2.0×SSC and about 65° C. In a particularly preferred embodiment, a nucleic acid of the present invention will specifically hybridize to one or more of the nucleic acid molecules set forth in SEQ ID NO:1 and SEQ ID NO: 2 or complements or fragments of either under high stringency conditions. In one aspect of the present invention, a preferred marker nucleic acid molecule of the present invention has the nucleic acid sequence set forth in SEQ ID NO: 1 and SEQ ID NO: 2 or complements thereof or fragments of either. In another aspect of the present invention, a preferred marker nucleic acid molecule of the present invention shares 80%, 81%, 82%, 83%, 84%, 85%, 86%, 87%, 88%, 89%, 90%, 912%, 92%, 93%, 94$, 95%, 96%, 97%, 98%, 99% and 100% sequence identity with the nucleic acid sequence set forth in SEQ ID NO: 1 and SEQ ID NO: 2 or complement thereof or fragments of either. In a further aspect of the present invention, a preferred marker nucleic acid molecule of the present invention shares 95% 96%, 97%, 98%, 99% and 100% sequence identity with the sequence set forth in SEQ ID NO: 1 and SEQ ID NO: 2 or complement thereof or fragments of either. SEQ ID NO: 1 and SEQ ID NO: 2 may be used as markers in plant breeding methods to identify the progeny of genetic crosses similar to the methods described for simple sequence repeat DNA marker analysis, in "DNA markers: Protocols, applications, and overviews: (1997) 173-

185, Cregan, et al., eds., Wiley-Liss NY; all of which is herein incorporated by reference. The hybridization of the probe to the target DNA molecule can be detected by any number of methods known to those skilled in the art, these can include, but are not limited to, fluorescent tags, radioactive tags, antibody based tags, and chemiluminescent tags.

Regarding the amplification of a target nucleic acid sequence (e.g., by PCR) using a particular amplification primer pair, "stringent conditions" are conditions that permit the primer pair to hybridize only to the target nucleic-acid sequence to which a primer having the corresponding wild-type sequence (or its complement) would bind and preferably to produce a unique amplification product, the amplicon, in a DNA thermal amplification reaction.

The term "specific for (a target sequence)" indicates that a probe or primer hybridizes under stringent hybridization conditions only to the target sequence in a sample comprising the target sequence.

As used herein, "amplified DNA" or "amplicon" refers to the product of nucleic-acid amplification of a target nucleic acid sequence that is part of a nucleic acid template. For example, to determine whether the soybean plant resulting from a sexual cross contains transgenic event genomic DNA from the soybean plant of the present invention, DNA extracted from a soybean plant tissue sample may be subjected to nucleic acid amplification method using a primer pair that includes a primer derived from flanking sequence in the genome of the plant adjacent to the insertion site of inserted heterologous DNA, and a second primer derived from the inserted heterologous DNA to produce an amplicon that is diagnostic for the presence of the event DNA. The amplicon is of a length and has a sequence that is also diagnostic for the event. The amplicon may range in length from the combined length of the primer pairs plus one nucleotide base pair, preferably plus about fifty nucleotide base pairs, more preferably plus about two hundred-fifty nucleotide base pairs, and even more preferably plus about four hundred-fifty nucleotide base pairs. Alternatively, a primer pair can be derived from flanking sequence on both sides of the inserted DNA so as to produce an amplicon that includes the entire insert nucleotide sequence. A member of a primer pair derived from the plant genomic sequence may be located a distance from the inserted DNA molecule, this distance can range from one nucleotide base pair up to about twenty thousand nucleotide base pairs. The use of the term "amplicon" specifically excludes primer-dimers that may be formed in the DNA thermal amplification reaction.

Nucleic-acid amplification can be accomplished by any of the various nucleic-acid amplification methods known in the art, including the polymerase chain reaction (PCR). A variety of amplification methods are known in the art and are described, inter alia, in U.S. Pat. Nos. 4,683,195 and 4,683,202 and in *PCR Protocols: A Guide to Methods and Applications*, ed. Innis et al., Academic Press, San Diego, 1990. PCR amplification methods have been developed to amplify up to 22 kb of genomic DNA and up to 42 kb of bacteriophage DNA (Cheng et al., Proc. Natl. Acad. Sci. USA 91:5695-5699, 1994). These methods as well as other methods known in the art of DNA amplification may be used in the practice of the present invention. The sequence of the heterologous DNA insert or flanking sequence from soybean event MON87754 with seed samples deposited as ATCC PTA-9385 can be verified (and corrected if necessary) by amplifying such sequences from the event using primers derived from the sequences provided herein followed by standard DNA sequencing of the PCR amplicon or of the cloned DNA.

The amplicon produced by these methods may be detected by a plurality of techniques. One such method is Genetic Bit Analysis (Nikiforov, et al. Nucleic Acid Res. 22:4167-4175, 1994) where an DNA oligonucleotide is designed which overlaps both the adjacent flanking genomic DNA sequence and the inserted DNA sequence. The oligonucleotide is immobilized in wells of a microwell plate. Following PCR of the region of interest (using one primer in the inserted sequence and one in the adjacent flanking genomic sequence), a single-stranded PCR product can be hybridized to the immobilized oligonucleotide and serve as a template for a single base extension reaction using a DNA polymerase and labelled ddNTPs specific for the expected next base. Readout may be fluorescent or ELISA-based. A signal indicates presence of the insert/flanking sequence due to successful amplification, hybridization, and single base extension.

Another method is the Pyrosequencing technique as described by Winge (Innov. Pharma. Tech. 00:18-24, 2000). In this method an oligonucleotide is designed that overlaps the adjacent genomic DNA and insert DNA junction. The oligonucleotide is hybridized to single-stranded PCR product from the region of interest (one primer in the inserted sequence and one in the flanking genomic sequence) and incubated in the presence of a DNA polymerase, ATP, sulfurylase, luciferase, apyrase, adenosine 5' phosphosulfate and luciferin. dNTPs are added individually and the incorporation results in a light signal which is measured. A light signal indicates the presence of the transgene insert/flanking sequence due to successful amplification, hybridization, and single or multi-base extension.

Fluorescence Polarization as described by Chen, et al., (Genome Res. 9:492-498, 1999) is a method that can be used to detect the amplicon of the present invention. Using this method an oligonucleotide is designed which overlaps the genomic flanking and inserted DNA junction. The oligonucleotide is hybridized to single-stranded PCR product from the region of interest (one primer in the inserted DNA and one in the flanking genomic DNA sequence) and incubated in the presence of a DNA polymerase and a fluorescent-labeled ddNTP. Single base extension results in incorporation of the ddNTP. Incorporation can be measured as a change in polarization using a fluorometer. A change in polarization indicates the presence of the transgene insert/flanking sequence due to successful amplification, hybridization, and single base extension.

TaqMan® (PE Applied Biosystems, Foster City, Calif.) is described as a method of detecting and quantifying the presence of a DNA sequence and is fully understood in the instructions provided by the manufacturer. Briefly, a FRET oligonucleotide probe is designed which overlaps the genomic flanking and insert DNA junction. The FRET probe and PCR primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the flanking/transgene insert sequence due to successful amplification and hybridization.

Molecular Beacons have been described for use in sequence detection as described in Tyangi, et al. (Nature Biotech. 14:303-308, 1996) Briefly, a FRET oligonucleotide probe is designed that overlaps the flanking genomic and insert DNA junction. The unique structure of the FRET probe results in it containing secondary structure that keeps the fluorescent and quenching moieties in close proximity. The FRET probe and PCR primers (one primer in the insert DNA sequence and one in the flanking genomic sequence) are cycled in the presence of a thermostable polymerase and dNTPs. Following successful PCR amplification, hybridization of the FRET probe to the target sequence results in the removal of the probe secondary structure and spatial separation of the fluorescent and quenching moieties that results in the production of a fluorescent signal. The fluorescent signal indicates the presence of the flanking/transgene insert sequence due to successful amplification and hybridization.

Other described methods, such as microfluidics (US Patent Pub. 2006068398, U.S. Pat. No. 6,544,734) provide methods and devices to separate and amplify DNA samples. Optical dyes are used to detect and quantitate specific DNA molecules (WO/05017181). Nanotube devices (WO/06024023) that comprise an electronic sensor for the detection of DNA molecules or nanobeads that bind specific DNA molecules and can then be detected.

DNA detection kits can be developed using the compositions disclosed herein and the methods well known in the art of DNA detection. The kits are useful for the identification of soybean event MON87754 DNA in a sample and can be applied to methods for breeding soybean plants containing the appropriate event DNA. The kits may contain DNA primers or probes that are homologous or complementary to SEQ ID NO: 1 through SEQ ID NO: 5 or DNA primers or probes homologous or complementary to DNA contained in the transgene genetic elements of DNA. These DNA sequences can be used in DNA amplification reactions or as probes in a DNA hybridization method. The sequences of the genomic DNA and transgene genetic elements contained in MON87754 soybean genome as illustrated in FIG. 2, consists of an expression cassette organized as follows: the nopaline left border sequence, followed by the gene cassette comprised of the promoter and leader sequence from the Glycine max 7S alpha' subunit of the beta-conglycinin storage protein (alpha'-bcsp) gene, which is upstream of the codon-optimized *Mortierella ramanniana* (also known as *Umbellopsis ramanniana*) diacylglycerol acyltransferase (MrDGAT2A.nno) (U.S. Pat. No. 6,822,141 incorporated by reference), which is upstream of the 3' UTR of the pea RbcS2 gene, followed by the octopine right border sequence (FIG. 2). DNA molecules useful as primers in DNA amplification methods can be derived from the sequences of the genetic elements of the transgene insert contained in the MON87754 event. These primer molecules can be used as part of a primer set that also includes a DNA primer molecule derived from the genome flanking the transgene insert of event MON87754 as presented in SEQ ID NO: 3 from bases 1 through 1002 and SEQ ID NO: 4 from bases 1 through 1244.

The soybean plant MON87754 was produced by an Agrobacterium mediated transformation process of an inbred soybean line with the plasmid construct pMON70900 (as shown in FIG. 1). The transformation method used is similar to that described in U.S. Pat. No. 5,914,451. The plasmid construct pMON70900 contains the linked plant expression cassettes with the regulatory genetic elements necessary for expression of the diacylglycerol acyltransferase proteins in soybean plant cells. Soybean cells were regenerated into intact soybean plants and individual plants were selected from the population of plants that showed integrity of the plant expression cassettes and an oil composition comprising an elevated oil level as compared to commodity soybean plants as well as a loss of the unlinked glyphosate resistance selection cassette. A soybean plant that contains in its genome the linked plant expression cassettes of pMON70900 is an aspect of the present invention.

The plasmid DNA inserted into the genome of soybean plant MON87754 was characterized by detailed molecular analyses. These analyses included: the insert number (number of integration sites within the soybean genome), the copy number (the number of copies of the T-DNA within one locus), and the integrity of the inserted gene cassettes. DNA molecular probes were used that included the intact diacylglycerol acyltransferase coding regions and their respective regulatory elements, the promoters, introns, and polyadenylation sequences of the plant expression cassettes, and the plasmid pMON70900 backbone DNA region. The data show that MON87754 contains a single T-DNA insertion with one copy of the diacylglycerol acyltransferase cassette. No additional elements from the transformation vector pMON70900, linked or unlinked to intact gene cassettes, were detected in the genome of MON87754. Finally, Inverse PCR and DNA sequence analyses were performed to determine the 5' and 3' insert-to-plant genome junctions, confirm the organization of the elements within the insert (FIG. 2), and determine the complete DNA sequence of the insert in soybean plant MON87754 (SEQ ID NO:5).

The following examples are included to demonstrate examples of certain preferred embodiments of the invention. It should be appreciated by those of skill in the art that the techniques disclosed in the examples that follow represent approaches the inventors have found function well in the practice of the invention, and thus can be considered to constitute examples of preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLES

Example 1

Transformation of Soybean A3525 with pMON70900 and Event Selection

The transgenic soybean plant MON87754 was generated by an Agrobacterium-mediated transformation of soybean cells with a DNA fragment derived from pMON70900 (FIG. 1). The binary plant transformation vector, pMON70900 contains two separate T-DNAs; one for expression of the MrDGAT2A.nno gene of interest, and the other for expression of the selectable marker CP4. The first T-DNA cassette utilizes the seed-specific promoter 7Sa' from Glycine max to drive the synthetic MrDGAT2A.nnp gene of interest followed by the E9 3'UTR element from *Pisium sativum* (FIGS. 1 and 2). The selectable marker T-DNA cassette carries CP4 driven by the Figwort Mosaic Virus 35S promoter and petunia hsp70 5'UTR with transit peptide EPSPS from *Arabidopsis thaliana* and also utilizes the E9 3'UTR element from *Pisium sativum* (FIG. 1). The cassette is flanked by left border and right border sequences at the 5' and 3' ends of the transformation cassette, respectively. An expression cassette (SEQ ID NO: 7) is used for the expression of the MrDGAT2A.nno gene. The cassette is organized as follows: the nopaline left border sequence, followed by the gene cassette comprised of the promoter and leader sequence from the Glycine max 7S alpha' subunit of the beta-conglycinin storage protein (alpha'-bcsp) gene, which is upstream of the codon-optimized *Mortierella ramanniana* (also known as *Umbellopsis ramanniana*) diacylglycerol acyltransferase 2A (MrDGAT2A.nno) (U.S. Pat. No. 6,822,141 incorporated by reference), which is upstream of the 3' UTR of the pea RbcS2 gene, followed by the octopine right border sequence (FIG. 2).

Explants transformed with pMON70900 were obtained via *Agrobacterium tumefaciens*-mediated transformation. Plants were regenerated from transformed tissue. Developing roots were sampled and assayed by PCR for the presence of the MrDGAT2A.nno using primers based upon the MrDGAT2A.nno cassette sequence (SEQ ID NO: 7). Approximately 577 R0 transformation events were produced and tested for the presence of a single-copy of the MrDGAT2A.nno cassette by Invader® (Third Wave Technologies, Inc., Madison, Wis.). In addition, linkage Southern blot analysis was used to determine the number of transgenic loci in each event. R0 events demonstrating a single-copy insertion of the MrDGAT2A.nno cassette were self pollinated to generate R1 seed. These events were grown in the greenhouse. Plants were sprayed with a sub-lethal dose of glyphosate to identify plants that had segregated away the CP4 selectable marker. Plants were also PCR assayed to verify absence of CP4 and presence of the MrDGAT2A.nno gene, and were assayed by Invader® to determine MrDGAT2A.nno copy number. Harvested R2 seed from homozygous, marker-free plants was analyzed via NIT for Oil and Protein. Events with >1% oil increase (as compared to negative segregant or parental control) and/or high DGAT enzyme activity were advanced to field trials. Based on these analyses, 10 events were selected to carry forward.

Southern analysis was performed on the ten selected R2 plants to confirm the presence of the expression cassette and absence of undesired nucleotide sequences from the transformation vector. Additionally the sequences flanking the MrDGAT2A.nno cassette insertion site for each event were determined. One progeny line designated event MON87754 was selected based upon its performance characteristics and molecular characterization.

Example 2

Isolation of Flanking Sequences Using Inverse PCR and Characterization of Transgenic Event GM_A36712

The characterization of the transgenic event GM_A36712 includes a determination of the transgene nucleotide sequence, the flanking nucleotide sequences, and the deletion or addition of nucleotide sequences as a result of the transgenic event. Typically, there are two junctions when there is one transgene insertion. The nucleotide sequence adjacent to the T-DNA left border is typically called the left flanking sequence. The nucleotide sequence adjacent to the T-DNA right border is typically called the right flanking sequence. In the transgenic event GM_A36712, the left flanking sequence corresponds to the 5' end of the transgene and the right flanking sequence corresponds to the 3' end of the transgene. In addition to the left and right flanking sequences, the characterization of the transgenic event GM_A36712 also includes a portion of wild type nucleotide sequence that was deleted during the T-DNA transfer and a fragment of nucleotide sequence that was added during the T-DNA transfer. The sequences that describe the left flanking nucleotides, the right flank nucleotides, the removed WT nucleotides, and the added nucleotides, together characterize the transgenic event GM_A36712 from the non-transgenic, background line A3525.

PCR and solid phase capture was used to determine the sequence of the left and the right flanking nucleotides. The PCR method used is a modification of a method called TAIL (Thermal Asymmetric InterLaced) PCR as described by Liu and Whittier (1995). Biotinylated primers to the T-DNA were used to capture and enrich for PCR products.

The DNA substrate used in the PCR reaction is the plant genomic DNA from the transgenic event GM_A36712. As long as there is enough DNA substrate relative to the other parts of the plant, any plant tissue at any stage of the plant's life cycle may be used. Preferably, plants are grown under green house conditions and leaf tissue is collected from young leaves. Plant genomic DNA can be further purified from plant tissue a number of ways. In this example, a hole punch sized piece of plant tissue was lyophilized and ground to a fine powder.

To the fine powder, a volume of 600 uL of extraction buffer was added and the suspension mixed in a paint shaker. The slurry was incubated for 1 hour at 65° C. The extraction buffer consisted of 1M KCl, 10 mM EDTA, and 100 mM Tris-HCl pH 8.0. This slurry can be used for the PCR, however, for this example, the DNA substrate was further purified by centrifugation for 1 minute at 1,500 rpm or 2,000 g equivalent. To the slurry, 200 ul of 5 M potassium acetate was added. The mixture was beat in a paint shaker, or equivalent, until the precipitation buffer was thoroughly mixed with the lysate. The non soluble fraction was separated by centrifugation for 10 minutes at a minimum of 3,000 rpm or 4,000 g equivalent. The DNA supernatant was transferred into a new container and room temperature isopropanol was added while maintaining a volumetric ratio of 6:5, supernatant to isopropanol. The solution was inverted 10 times and let sit at room temperature for 10 minutes to precipitate the DNA. The DNA precipitant was separated by centrifugation for 10 minutes at a minimum of 3,000 rpm or 4,000 g equivalent resulting in a pellet of enriched DNA. The supernatant was poured off and 200 ul of 70% ethanol wash was added. The pellet and wash was incubated at room temperature for 3 to 5 minutes. The pellet was subjected to another centrifugation for 5 minutes at a minimum of 3,000 rpm or 4,000 g equivalent to keep the pellet of DNA from sliding off the bottom of the container. The supernatant was removed without perturbing the DNA pellet. The DNA pellet was dried at 65° C. for 30 minutes when all liquid had evaporated. The DNA pellet was reconstituted in 200 ul of 1× TE buffer by letting it sit at room temperature for 30 minutes. The pellet was resuspended by beating it for 60 seconds in a paint shaker, or equivalent. The solution can be stored at 4° C.

An aliquot of DNA purified in this manner was subjected to a battery of PCR reactions. Each PCR reaction used a biotinylated primer designed to anneal to a T-DNA sequence near the expected junction and to extend past the junction into the flanking sequence during PCR. Each reaction also used a primer designed to anneal to a flanking sequence near the expected junction and to extend past the junction into the transgene during PCR. The PCR conditions are similar to Liu and Whittier (1995) PCR conditions for TAIL PCR with the following modifications to the primary PCR: The 10 reduced stringency cycles were omitted. The 12 super cycles were increased to 15 super cycles. After the primary PCR, PCR products were captured on a streptavidin or equivalent solid phase substrate. A second PCR reaction was performed similar to Liu and Whittier (1995) PCR conditions for TAIL PCR with the following modifications to the secondary PCR: The 10 super cycles were increased to 12 super cycles and 20 normal cycles were added at the end of the PCR to maximize the generation of template.

The PCR template amplified in this way was sequenced to determine the sequence of the transgene and flanking nucleotides around each junction. Using different random primer and T-DNA primer combinations, various sized PCR templates are amplified and various length flanking sequence elucidated for each flank providing for higher coverage and lengthier coverage. The 5' flanking sequence which extends into the left border sequence of the cassette T-DNA is presented as SEQ ID NO: 3 ([C], see FIG. 2). The 3' flanking sequence which extends into the right border sequence of the MrDGAT2A.nno cassette T-DNA is presented as SEQ ID NO: 4 ([D], see FIG. 2). The portion of the MrDGAT2A.nno cassette DNA (SEQ ID NO: 7) from pMON70900 that was fully integrated into the A3525 genomic DNA is presented as SEQ ID NO: 5 ([E], see FIG. 2).

Isolated sequences were compared to the T-DNA sequence to identify the flanking sequence and the co-isolated T-DNA fragment. Confirmation of the presence of the expression cassette was achieved by PCR with primers designed based upon the deduced flanking sequence data and the known T-DNA sequence. The A3525 wild type sequence corresponding to the same region in which the T-DNA was integrated in the transformed line was isolated using primers designed from the flanking sequences in GM_A36712. The flanking sequences in GM_A36712 and the A3525 wild type sequence were analyzed against multiple nucleotide and protein databases. This information was used to examine the relationship of the transgene to the plant genome and to look at the insertion site integrity. Compared to the wild type sequence, it was deduced that twenty-two (22) nucleotides from the wild type allele were deleted and replaced by the trangene and by nine (9) additional nucleotides that were added at the left border junction. The flanking sequence and wild type sequences were used to design primers for TaqMan endpoint assaysm which are used to identify the events and determine zygosity as described in Example 3.

Example 3

Event-Specific Endpoint TaqMan and Zygosity Assays

The methods used to identify event MON87754 in a sample are described in an event-specific endpoint TaqMan PCR for which examples of conditions are described in Table 1 and Table 2. The DNA primers used in the endpoint assay are primers SQ20209 (SEQ ID NO: 8), SQ20331 (SEQ ID NO: 9) and 6FAM™ labeled primer PB10090 (SEQ ID NO: 10). 6FAM™ is a fluorescent dye product of Applied Biosystems (Foster City, Calif.) attached to the DNA primer. For TaqMan MGB (Minor Groove Binding) probes, the 5'exonuclease activity of Taq DNA polymerase cleaves the probe from the 5'-end, between the fluorophore and quencher. When hybridized to the target DNA strand, quencher and fluorophore are separated enough to produce a fluorescent signal.

SQ20209 (SEQ ID NO: 8) and SQ20331 (SEQ ID NO: 9) when used as described with PB10090 (SEQ ID NO: 10) produce a DNA amplicon that is diagnostic for event MON87754 DNA. The controls for this analysis should include a positive control from soybean known to contain event MON87754 DNA, a negative control from non-transgenic soybean and a negative control that contains no template DNA.

These assays are optimized for use with an Applied Biosystems GeneAmp PCR System 9700, Stratagene Robocycler, MJ Engine, Perkin-Elmer 9700 or Eppendorf Mastercycler Gradient thermocycler. Other methods and apparatus may be known to those skilled in the art to produce amplicons that identify the event MON87754 DNA.

DNA amplification in a Stratagene Robocycler, MJ Engine, Perkin-Elmer 9700, Eppendorf Mastercycler Gradient thermocycler, Applied Biosystems GeneAmp PCR System 9700 or MJ Research DNA Engine PTC-225 thermal cycler is performed using the following cycling parameters. When running the PCR in the Eppendorf Mastercycler Gradient or MJ Engine, the thermocycler should be run in the calculated mode. When running the PCR in the Perkin-Elmer 9700, the thermocycler is run with the ramp speed set at maximum.

TABLE 1

Soybean MON87754 Event Specific Endpoint TaqMan PCR

| Step | Reagent | Volume | Comments |
|---|---|---|---|
| 1 | 18 megohm water | adjust for final volume of 10 ul | |
| 2 | 2X Universal Master Mix (Contains dNTPs, enzyme and buffer) | 5.0 ul | 1X final concentration of dNTPs, enzyme and buffer |
| 3 | Primer-1 and Primer-2 Mix (resuspended in 18 megohm water to a concentration of 20 uM for each primer) Example: In a microcentrifuge tube, the following should be added to achieve 500 ul at a final concentration of 20 uM: 100 ul of Primer SQ20209 at a concentration of 100 uM 100 ul of Primer SQ20331 at a concentration of 100 uM 300 ul of 18 megohm water | 0.5 ul | 1.0 uM final concentration |
| 4 | Event 6-FAM ™ MGB Probe PB10090 (resuspended in 18 megohm water to a concentration of 10 uM) Note: 6-FAM ™ MGB probe is light sensitive | 0.2 ul | 0.2 uM final concentration |
| 5 | Extracted DNA (template): Leaf samples to be analyzed Negative control (non-transgenic DNA) Negative water control (no template control) Positive control Homozygous GM_A36712 DNA Positive control Hemizygous GM_A36712 DNA | 3.0 ul | |

TABLE 2

Endpoint TaqMan thermocycler conditions

| Cycle No. | Settings |
|---|---|
| 1 | 50° C. 2 minutes |
| 1 | 95° C. 10 minutes |
| 10 | 95° C. 15 seconds |
| | 64° C. 1 minute |
| | −1° C./cycle |
| 30 | 95° C. 15 seconds |
| | 54° C. 1 minute |
| 1 | 10° C. Forever |

Determining zygosity for event MON87754 in a sample was done using an event-specific zygosity endpoint TaqMan PCR for which examples of conditions are described in Table 3 and Table 4. The DNA primers used in the zygosity assay are primers SQ20209 (SEQ ID NO: 8), SQ20331 (SEQ ID NO: 9), SQ20332 (SEQ ID NO: 11), 6FAM™ labeled primer PB100909 (SEQ ID NO: 10) and VIC™ labeled primer PB10091 (SEQ ID NO: 12). 6FAM™ and VIC™ are fluorescent dye products of Applied Biosystems (Foster City, Calif.) attached to the DNA primers.

SQ20209 (SEQ ID NO: 8) and SQ20331 (SEQ ID NO: 9) when used in these reaction methods with PB10090 (SEQ ID NO: 10) produce a DNA amplicon that is diagnostic for event MON87754 DNA. The controls for this analysis should include a positive control from soybean containing event MON87754 DNA, a negative control from non-transgenic soybean and a negative control that contains no template DNA.

SQ20209 (SEQ ID NO: 8) and SQ20332 (SEQ ID NO: 11) when used in these reaction methods with PB10091 (SEQ ID NO: 12) produce a DNA amplicon that is diagnostic for the wild type allele.

Heterozygosity is determined by the presence of both amplicons demonstrated by the liberation of fluorescent signal from both probes PB10090 and PB10091.

These assays are optimized for use with an Applied Biosystems GeneAmp PCR System 9700, Stratagene Robocycler, MJ Engine, Perkin-Elmer 9700 or Eppendorf Mastercycler Gradient thermocycler. Other methods and apparatus known to those skilled in the art that produce amplicons that identify the event MON87754 DNA is within the skill of the art.

DNA amplification in a Stratagene Robocycler, MJ Engine, Perkin-Elmer 9700, Eppendorf Mastercycler Gradient thermocycler, Applied Biosystems GeneAmp PCR System 9700 or MJ Research DNA Engine PTC-225 thermal cycler is performed using the following cycling parameters. When running the PCR in the Eppendorf Mastercycler Gradient or MJ Engine, the thermocycler should be run in the calculated mode. When running the PCR in the Perkin-Elmer 9700, the thermocycler is run with the ramp speed set at maximum.

TABLE 3

Soybean MON87754 Event-Specific Zygosity Endpoint TaqMan PCR

| Step | Reagent | Volume | Comments |
|---|---|---|---|
| 1 | 18 megohm water | adjust for final volume of 10 ul | |
| 2 | 2X Universal Master Mix (Contains dNTPs, enzyme and buffer) | 5.0 ul | 1X final concentration of dNTPs, enzyme and buffer |
| 3 | Zygosity Primer-1, Primer-2, & Primer-3 Mix (resuspended in 18 megohm water to a concentration of 20 uM for each primer) Example: In a microcentrifuge tube, the following should be added to achieve 500 ul at a final concentration of 20 uM: 100 ul of Primer SQ20209 at a concentration of 100 uM 100 ul of Primer SQ20331 at a concentration of 100 uM 100 ul of Primer SQ20332 at a concentration of 100 uM 200 ul of 18 megohm water | 0.5 ul | 1.0 uM final concentration |
| 4 | Event 6-FAM ™ MGB Probe PB10090 (resuspended in 18 megohm water to a concentration of 10 uM) | 0.2 ul | 0.2 uM final concentration |
| 5 | WT VIC ™ MGB Probe PB10091 (resuspended in 18 megohm water to a concentration of 10 uM) | 0.2 ul | 0.2 uM final concentration |
| 6 | Extracted DNA (template): 1. Leaf Samples to be analyzed 2. Negative control (non-transgenic DNA) 3. Negative water control (no template control) 4. Positive control Homozygous MON87754 DNA 5. Positive control Hemizygous MON87754 DNA | 3.0 ul | |

TABLE 4

Zygosity Endpoint TaqMan thermocycler conditions

| Cycle No. | Settings |
|---|---|
| 1 | 50° C. 2 minutes |
| 1 | 95° C. 10 minutes |
| 10 | 95° C. 15 seconds |
| | 64° C. 1 minute |
| | −1° C./cycle |
| 30 | 95° C. 15 seconds |
| | 54° C. 1 minute |
| 1 | 10° C. Forever |

Example 4

Identification of Event MON87754 in any MON87754 Breeding Event

The following example describes how one may identify the MON87754 event within progeny of any breeding event containing MON87754 soybean.

DNA event primer pairs are used to produce an amplicon diagnostic for soybean event MON87754. An amplicon diagnostic for MON87754 comprises at least one junction sequence, SEQ ID NO: 1 or SEQ ID NO: 2 ([A] and [B], respectively as illustrated in FIG. 2). SEQ ID NO: 1 ([A] of FIG. 2) is a nucleotide sequence corresponding to the junction of the 5' flanking sequence (positions 942 through 951 of SEQ ID NO: 3 [C], see FIG. 2) and the integrated left border of the MrDGAT2A.nno cassette (positions 1 through 10 of SEQ ID NO: 5 [E], see FIG. 2). SEQ ID NO: 2 ([B], see FIG. 2) is a nucleotide sequence corresponding to the junction of the integrated right border of the MrDGAT2A.nno cassette (positions 3027 through 3036 of SEQ ID NO: 5 [E], see FIG. 2) and the 3' flanking sequence (positions 1 through 10 of SEQ ID NO: 4 [D], see FIG. 2).

Event primer pairs that will produce a diagnostic amplicon for MON87754 include primer pairs based upon the flanking sequences and the inserted MrDGAT2A.nno cassette. To acquire a diagnostic amplicon in which at least 11 nucleotides of SEQ ID NO: 1 is found, one would design a forward primer based upon SEQ ID NO: 3 from bases 1 through 942 and a reverse primer based upon the inserted expression MrDGAT2A.nno cassette, SEQ ID NO: 5 from positions 10 through 3036. To acquire a diagnostic amplicon in which at least 11 nucleotides of SEQ ID NO: 2 is found, one would design a forward primer based upon the inserted MrDGAT2A.nno cassette, SEQ ID NO: 5, from positions 10 through 3027 and a reverse primer based upon the 3' flanking sequence, SEQ ID NO: 4, from bases 154 through 1244. For practical purposes, one should design primers which produce amplicons of a limited size range, preferably between 200 to 1000 bases. Smaller sized amplicons in general are more reliably produced in PCR reactions, allow for shorter cycle times and can be easily separated and visualized on agarose gels or adapted for use in endpoint TaqMan-like assays. In addition, amplicons produced using said primer pairs can be cloned into vectors, propagated, isolated and sequenced or can be sequenced directly with methods well established in the art. Any primer pair derived from the combination of SEQ ID NO: 3 and SEQ ID NO: 5 or the combination of SEQ ID NO: 4 and SEQ ID NO: 5 that are useful in a DNA amplification method to produce an amplicon diagnostic for MON87754 or progeny thereof is an aspect of the present invention. Any single isolated DNA polynucleotide primer molecule comprising at least 11 contiguous nucleotides of SEQ ID NO: 3, or its complement that is useful in a DNA amplification method to produce an amplicon diagnostic for MON87754 or progeny thereof is an aspect of the present invention. Any single isolated DNA polynucleotide primer molecule comprising at least 11 contiguous nucleotides of SEQ ID NO: 4, or its complement that is useful in a DNA amplification method to produce an amplicon diagnostic for MON87754 or progeny thereof is an aspect of the present invention. Any single isolated DNA polynucleotide primer molecule comprising at least 11 contiguous nucleotides of SEQ ID NO: 5, or its complement that is useful in a DNA amplification method to produce an amplicon diagnostic for MON87754 or progeny thereof is an aspect of the present invention.

An example of the amplification conditions for this analysis is illustrated in Table 5 and Table 6. However, any modification of these methods or the use of DNA primers homologous or complementary to SEQ ID NO: 3 or SEQ ID NO: 4 or DNA sequences of the genetic elements contained in the transgene insert (SEQ ID NO: 5) of MON87754 that produce an amplicon diagnostic for MON87754, is within the art. A diagnostic amplicon comprises a DNA molecule homologous or complementary to at least one transgene/genomic junction DNA (SEQ ID NO: 1 or SEQ ID NO: 2), or a substantial portion thereof.

An analysis for event MON87754 plant tissue sample should include a positive tissue control from event MON87754, a negative control from a soybean plant that is not event MON87754, for example, but not limited to A3525, and a negative control that contains no soybean genomic DNA. A primer pair that will amplify an endogenous soybean DNA molecule will serve as an internal control for the DNA amplification conditions. Additional primer sequences can be selected from SEQ ID NO: 3, SEQ ID NO: 4, or SEQ ID NO: 5 by those skilled in the art of DNA amplification methods, and conditions selected for the production of an amplicon by the methods shown in Table 5 and Table 6 may differ, but result in an amplicon diagnostic for event MON87754 DNA. The use of these DNA primer sequences with modifications to the methods of Table 5 and Table 6 are within the scope of the invention. The amplicon produced by at least one DNA primer sequence derived from SEQ ID NO: 3, SEQ ID NO: 4, or SEQ ID NO: 5 that is diagnostic for MON87754 is an aspect of the invention.

DNA detection kits that contain at least one DNA primer derived from SEQ ID NO: 3, SEQ ID NO: 4, or SEQ ID NO: 5, that when used in a DNA amplification method, produces a diagnostic amplicon for MON87754 or its progeny is an aspect of the invention. A soybean plant or seed, wherein its genome will produce an amplicon diagnostic for MON87754 when tested in a DNA amplification method is an aspect of the invention. The assay for the MON87754 amplicon can be performed by using an Applied Biosystems GeneAmp PCR System 9700, Stratagene Robocycler, MJ Engine, Perkin-Elmer 9700 or Eppendorf Mastercycler Gradient thermocycler or any other amplification system that can be used to produce an amplicon diagnostic of MON87754 as shown in Table 6.

TABLE 5

Soybean MON87754 Event Specific PCR Assay

| Step | Reagent | Volume | Comments |
|---|---|---|---|
| 1 | 18 megohm water | adjust for final volume of 10 ul | |
| 2 | 2X Universal Master Mix (Contains dNTPs, enzyme and buffer) | 5.0 ul | 1X final concentration of dNTPs, enzyme and buffer |
| 3 | Primer-1 and Primer-2 Mix (resuspended in 18 megohm water to a concentration of 20 uM for each primer) Example: In a microcentrifuge tube, the following should be added to achieve 500 ul at a final concentration of 20 uM: 100 ul of Primer 1 at a concentration of 100 uM 100 ul of Primer 2 at a concentration of 100 uM 300 ul of 18 megohm water | 0.5 ul | 1.0 uM final concentration |
| 5 | Extracted DNA (template) 50 ng of genomic DNA: Leaf samples to be analyzed Negative control (non-transgenic DNA) Negative water control (no template control) Positive control MON87754 DNA | 3.0 ul | |

TABLE 6

Soybean MON87754 Event Thermocycler Conditions

| Cycle No. | Settings |
|---|---|
| 1 | 50° C. 2 minutes |
| 1 | 95° C. 10 minutes |
| 10 | 95° C. 15 seconds |
| | 64° C. 1 minute |
| | −1° C./cycle |

TABLE 6-continued

Soybean MON87754 Event Thermocycler Conditions

| Cycle No. | Settings |
|---|---|
| 30 | 95° C. 15 seconds |
|  | 54° C. 1 minute |
| 1 | 10° C. Forever |

A deposit of the, soybean event MON87754 seed disclosed above and recited in the claims, has been made under the Budapest Treaty with the American Type Culture Collection (ATCC), 10801 University Boulevard, Manassas, Va. 20110. The ATCC accession number is PTA-9385. The deposit will be maintained in the depository for a period of 30 years, or 5 years after the last request, or for the effective life of the patent, whichever is longer, and will be replaced as necessary during that period.

Having illustrated and described the principles of the present invention, it should be apparent to persons skilled in the art that the invention can be modified in arrangement and detail without departing from such principles. We claim all modifications that are within the spirit and scope of the appended claims.

LITERATURE CITED AND INCORPORATED BY REFERENCE

These References are Specifically Incorporated by Reference Relevant to the Supplemental Procedural or Other Details that they Provide 1. Cahoon, E. B. et al., Engineering oilseeds for sustainable production of industrial and nutritional feedstocks: solving bottlenecks in fatty acid flux. *Current Opinion in Plant Biol.* 10, 236-244 (2007).
2. Cases, S. et al. Identification of a gene encoding an acyl CoA:diacylglycerol acyltransferase, a key enzyme in triacylglycerol synthesis. *Proc. Natl. Acad. Sci.* 95, 13018-13023, (1998).
3. Chen, Z-L., Schuler, M A, Beachy, R. N., Functional analysis of regulatory elements in a plant embryo-specific gene. *Proc. Natl. Acad. Sci.,* 83, 8560-8564 (1986).
4. Harwood, J. L. Recent advances in the biosynthesis of plant fatty acids. *Biochem. Biophys. Acta.* 1301, 7-56, (1996).
5. He, X., Chen, GQ, Lin, J-T, McKeon, TA, Regulation of diacylglycerol acyltransferase in developing seeds of castor. *Lipids,* 39, 865-871 (2005).
6. Kroon, J. T. M., Wei, W, Simon, W J, Slabas, A R, Identification and functional expression of a type 2 acyl-CoA: diacylglycerol acyltransferase (DGAT2) in developing castor bean seeds which has high homology to the major triglyceride biosynthetic enzyme of fungi and animals. *Phytochem.* 67, 2541-2549 (2006).
7. Lardizabal, K. DGAT2 Is a New Diacylglycerol Acyltransferase Gene Family. *J. Biol. Chem.* 276, 38862-38869 (2001).
8. Lardizabal, K., Hawkins, D, Thompson, G. Diacylglycerol acyl transferase proteins. U.S. Pat. No. 7,135,617 (2006).
9. Lardizabal, K., Effertz, R., Pedroso, M. C., Levering, C., Mai, J., Jury, T., Gruys, K., and Bennett, K. Expression of *U. ramanniana* DGAT2A in Seed Increases Oil in Soybean. Publication pending
10. Routaboul, J. M., Benning, C, Bechtold, N, Caboche, M, and Lepiniec, L., The TAG1 locus of Arabidopsis encodes for a diacylglycerol acyltransferase. *Plant Physiol. Biochem.* 37, 831-840 (1999).
11. Sambrook, J., E. F. Frisch, and T. Maniatis. 1989. Molecular cloning: A laboratory manual. Cold Spring Harbor Press, Cold Spring Harbor, N.Y.
12. Shockey, J. M. et al. Tung tree DGAT1 and DGAT2 have nonredundant functions in triacylglycerol biosynthesis and are localized to different subdomains of the endoplasmic reticulum. *Plant Cell,* 18 (9), 2294-2313 (2006).
13. Turkish, A. and Sturley, S., Regulation of triglyceride metabolism I. Eukaryotic neutral lipid synthesis: "Many ways to skin ACAT or a DGAT". *Am. J. Physiol. Gastrointest. Liver Physiol.* 292, G953-G957, (2007).
14. Westlake, R. et al., Developmental profile of diacylglycerol acyltransferase in maturing seeds of oilseed rape and safflower and microspore-derived cultures of oilseed rape. *Plant Physiol.* 102, 565-571 (1993).
15. Yen, C-L. E, Stone, S J, Cases, S, Zhou, P, Farese, R V, Identification of a gene encoding MGAT1, a monoacylglycerol acyltransferase. *Proc. Natl. Acad. Sci.,* 99, 8512-8517 (2002).
16. Yen, C-L. E, Brown, C H, Monetti, M, Farese, R V, A human skin multifunctional O-acyltransferase that catalyzes the synthesis of acylglycerols, waxes and retinyl esters. *J Lipids Rsch.* 46, 2388-2397 (2005).
17. Zou, J. T. et al., The *Arabidopsis thaliana* TAG1 mutant has a mutation in a diacylglycerol acyltransferase gene, *Plant J.* 19, 645-653 (1999).
18. Liu and Whittier (1995). Thermal asymmetric interlaced PCR: automatable amplification and sequencing of insert end fragments from P1 and YAC clones for chromosome walking. Genomics Vol. 25, pp 674-681.

We claim:

1. A method of detecting the presence of a soybean event MON87754 nucleotide sequence in a biological sample, the method comprising:
   i. contacting the sample with a DNA primer pair of sufficient length of contiguous nucleotides of SEQ ID NO: 6 or its full complement, wherein said pair is capable of producing an amplicon diagnostic for event MON87754;
   ii. performing a nucleic acid amplification reaction, thereby producing an amplicon; and
   iii. detecting said amplicon, wherein said amplicon comprises SEQ ID NO: 1 or SEQ ID NO: 2.

2. The method of claim 1, wherein said DNA primer pair comprises a first primer comprising a sequence of at least 11 consecutive nucleotides of SEQ ID NO: 3 or its complement, and a second primer comprising a sequence of at least 11 consecutive nucleotides of SEQ ID NO: 5 or its complement.

3. The method of claim 1, wherein said DNA primer pair comprises a first primer comprising a sequence of at least 11 consecutive nucleotides of SEQ ID NO: 4 or its complement, and a second primer comprising a sequence of at least 11 consecutive nucleotides of SEQ ID NO: 5 or its complement.

4. A transgenic soybean plant, or parts thereof, comprising DNA encoding a *Mortierella ramanniana* diacylglycerol acyltransferase 2A (MrDGAT2A) and DNA having the nucleotide sequences of SEQ ID NO: 1 and SEQ ID NO: 2.

5. A polynucleotide comprising a nucleotide sequence selected from the group consisting of SEQ ID NO: 1, SEQ ID NO: 2, and the full-length complements thereof.

6. A method of detecting the presence of a soybean event MON87754 polynucleotide in a biological sample, the method comprising:
   i. contacting the sample with a probe comprising SEQ ID NO: 1, SEQ ID NO: 2, or the full-length complement thereof; and
   ii. detecting binding of said probe to said sample, wherein detection of binding is diagnostic for the presence of said soybean event MON87754 polynucleotide in said sample.

7. A composition derived from the transgenic soybean plant, or parts thereof, of claim 4, wherein said composition comprises a detectable amount of said DNA encoding said MrDGAT2A and said DNA having the nucleotide sequences of SEQ ID NO: 1 and SEQ ID NO: 2, wherein said composition is a commodity product selected from the group consisting of soybean meal, soy flour, soy protein concentrate, soy protein isolates, texturized soy protein concentrate, hydrolyzed soy protein and whipped topping.

8. A transgenic soybean seed comprising DNA encoding a *Mortierella ramanniana* diacylglycerol acyltransferase 2A (MrDGAT2A) and DNA having the nucleotide sequences of SEQ ID NO: 1 and SEQ ID NO: 2.

9. The polynucleotide of claim 5, wherein said polynucleotide is labeled with at least one fluorophore, radioactive isotope, ligand, or chemiluminescent agent.

10. The transgenic soybean plant, or parts thereof, of claim 4, comprising a DNA molecule consisting of the nucleotide sequence of SEQ ID NO: 3 from positions 1 to 950, the nucleotide sequence of SEQ ID NO: 5 from positions 1 to 3036, and the nucleotide sequence of SEQ ID NO: 4 from positions 144 to 1244.

11. The transgenic soybean plant, or parts thereof, of claim 4, comprising a DNA molecule consisting of the nucleotide sequence of SEQ ID NO: 6 from positions 1 to 5087.

12. The transgenic soybean seed of claim 8, comprising a DNA molecule consisting of the nucleotide sequence of SEQ ID NO: 3 from positions 1 to 950, the nucleotide sequence of SEQ ID NO: 5 from positions 1 to 3036, and the nucleotide sequence of SEQ ID NO: 4 from positions 144 to 1244.

13. The transgenic soybean seed of claim 8, comprising a DNA molecule consisting of the nucleotide sequence of SEQ ID NO: 6 from positions 1 to 5087.

14. Seed of soybean plant designated MON87754, having representative sample deposited with the American Type Culture Collection (ATCC) under Accession No. PTA-9385.

15. A soybean plant MON87754, or parts thereof, produced by growing the seed of claim 14.

16. A soybean plant, seed, or parts thereof, comprising soybean event MON87754.

* * * * *

SEQUENCE LISTING

```
<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: 5' junction sequence

<400> SEQUENCE: 1
tttaaggatc tctacatgga                                              20

<210> SEQ ID NO 2
<211> LENGTH: 20
<212> TYPE: DNA
```

-continued

<213> ORGANISM: Artificial Sequence
<220> FEATURE:
<223> OTHER INFORMATION: 3' junction sequence

<400> SEQUENCE: 2

```
atcagtgttt tccatcatac                                                  20
```

<210> SEQ ID NO 3
<211> LENGTH: 1002
<212> TYPE: DNA
<213> ORGANISM: Glycine max

<400> SEQUENCE: 3

```
tcactcaacc agtcaatatg atcaatacac aagtgttatg caataaatat actaagactc      60
aatcttatat gcaatgtggt accatgtcaa tgaaaaacct cttcgagcgc ctaggagtac     120
atgacaagac agaccacaca ctagtaagtc aggtcactct cactaggtaa atcataggg      180
agactagtca ggatcacatt gttttgtgag aatgcttcaa ctatgtagga ttggcacata    240
cttaaatgaa cattcaaatc aggagtattt accccaagg cctagactcc gaagagtcca     300
gtagggtctc tccttcctta ttcaagttca acccaaaaaa tattttaaca catagactct    360
atctatgaac tgtacaaaac acgactttt caattgttc tcaaaatagt tttatctcgt      420
tacacctcaa agtgattaaa ctcatcgggt tcccataatg gttcccatca caatactcgt    480
tgcacattaa cttgtcgccc ttaaagggtc ttacagtcat gtgattgtat ggttcgtagc    540
tcataactca atgcacacaa tatctcaata cacatgtatt tcataattca tcacatattc    600
aatttatcac ttcaacacaa tttcaatcac aatttcatga tcccaatata ataatttatc   660
atgctaatct agtaaatctt gtccaacaca acaaattat ataaaaatgt ttctcataac    720
atgagggta aaaaccctca acaatttca cataatcata tgaaaatcaa aggaataaaa      780
tcataggtca aaaacacaaa acaccaata atactcaatt ttatcaatca attcgcatca    840
ggacatcaat tgactcgtca aacacaacaa tatcgtaatt aaaatcgtaa aagaagaatt    900
ctaattcaat aaatatctca aaataaatta taatttaatc atttaaggat ctctacatgg    960
atcagcaatg agtatgatgg tcaatatgga gaaaagaaaa ga                       1002
```

<210> SEQ ID NO 4
<211> LENGTH: 1244
<212> TYPE: DNA
<213> ORGANISM: Glycine max

<400> SEQUENCE: 4

```
tttaatgcat tttatgactt gccaattgat tgacaacatg catcaatcga ccgtaccgcg     60
gccgctcgag caggacctgc agaagctagc ttgatgggga tcagattgtc gtttcccgcc   120
ttcagtttaa actatcagtg ttttccatca tactcattgc gataaaatgt aaaaatggac   180
ctaatatatc tatatttata gttagagtac ttcctttcta ttatttactt tattttttta    240
ttttattatt ttataacaca aaaatttatg ttattcccta tcaaattaat aaataaaaca    300
ttatttttat tttttaataa catatattta ttttattat cttaaaatta ttattttaat     360
taataaaact atctcttctt atttatttaa ttataaaatt ttcattattt tcttttaaact   420
ttttttatt tttaaataaa atcatttta atttatttca cgagaaatga aatgttacat     480
tatccactat ttatcctaaa cccataaaat atcatattca ctggaggctt tttgctaact    540
aaaataaaaa aatccatcac tttattttc aatgaccggt cctttaataa tctcataaag    600
taaacttact ttttaatatc aaaatttgac attaaattat atagggaac catttttaatg   660
```

| | |
|---|---|
| taaaataaat tatattaaaa gatcacttta ttttcaaaaa ttgatctttt tttgtaggtg | 720 |
| taaaaaatat tctttgattg ataacttctc tgaaaaataa taaagatcac taaaacatta | 780 |
| cttttatcaa taaaattctt ttttatgcat atatttctgg ttatttcaga aactgaaatc | 840 |
| aaaagtatca catactacta tatatttttt attactttt cttgtgtaca tatatttact | 900 |
| attactgtaa ctaaatggtt ttaaaggtag ataaaaaaaa actaatgatt ttaaagaaag | 960 |
| agatatatat ttagtttttt aattatttgc tgttgatggg tgggttgcgt atgacgtgtg | 1020 |
| attattctat actataataa cgtttcgctt ttggaggaaa tgtttcttgc tgcgcacggg | 1080 |
| tacacgtaca attatacaac cagatcatca ctctgaaggg acaaaagaaa caaaggcata | 1140 |
| aaaaaacaca taaccaaaac cagccatttc gtagttatga agagttgcag gaagttgaag | 1200 |
| cgttgcagat gggtgaaaac agtggacagt ggctctacat cgac | 1244 |

<210> SEQ ID NO 5
<211> LENGTH: 3036
<212> TYPE: DNA
<213> ORGANISM: Glycine max

<400> SEQUENCE: 5

| | |
|---|---|
| tctacatgga tcagcaatga gtatgatggt caatatggag aaaaagaaag agtaattacc | 60 |
| aattttttt caattcaaaa atgtagatgt ccgcagcgtt attataaaat gaaagtacat | 120 |
| tttgataaaa cgacaaatta cgatccgtcg tatttatagg cgaaagcaat aaacaaatta | 180 |
| ttctaattcg gaaatcttta tttcgacgtg tctacattca cgtccaaatg ggggcttaga | 240 |
| tgagaaactt cacgatttgg cgcgccaaag cttgatatcg aattcctgca gccccttaa | 300 |
| ttaaggggg gatccactag ttctagagga tccccggcaa aaacatttaa tacgtattat | 360 |
| ttaagaaaaa aatatgtaat aatatatttta tattttaata tctattctta tgtatttttt | 420 |
| aaaaatctat tatatattga tcaactaaaa tattttata tctacactta ttttgcattt | 480 |
| ttatcaattt tcttgcgttt tttggcatat ttaataatga ctattcttta ataatcaatc | 540 |
| attattctta catggtacat attgttggaa ccatatgaag tgtccattgc atttgactat | 600 |
| gtggatagtg ttttgatcca ggcctccatt tgccgcttat taattaattt ggtaacagtc | 660 |
| cgtactaatc agttacttat ccttcctcca tcataattaa tcttggtagt ctcgaatgcc | 720 |
| acaacactga ctagtctctt ggatcataag aaaaagccaa ggaacaaaag aagacaaaac | 780 |
| acaatgagag tatcctttgc atagcaatgt ctaagttcat aaaattcaaa caaaaacgca | 840 |
| atcacacaca gtggacatca cttatccact agctgatcag gatcgccgcg tcaagaaaaa | 900 |
| aaaactggac cccaaaagcc atgcacaaca acacgtactc acaaaggtgt caatcgagca | 960 |
| gcccaaaaca ttcaccaact caacccatca tgagcccaca catttgttgt ttctaaccca | 1020 |
| acctcaaact cgtattctct tccgccacct catttttgtt tatttcaaca cccgtcaaac | 1080 |
| tgcatgccac cccgtggcca aatgtccatg catgttaaca agacctatga ctataaatat | 1140 |
| ctgcaatctc ggcccaggtt ttcatcatca agaaccgggt accgggccgc accatggcta | 1200 |
| gcaaggacca gcacctccaa cagaaggtga agcacaccct tgaggccatc ccatccccta | 1260 |
| ggtatgctcc actcagggtc ccacttagga gaaggctcca aacccttgct gttctcctct | 1320 |
| ggtgctccat gatgagcatc tgcatgttca tcttcttctt cctctgcagc atccctgtgc | 1380 |
| tcctttggtt cccaattatc ctctacttga cctggatttt ggtgtgggat aaggcccctg | 1440 |
| agaacggagg cagacctatc aggtggctca ggaacgcagc ttggtggaag ctctttgctg | 1500 |

-continued

```
gatacttccc agctcatgtt atcaaggagg ctgaccttga cccatccaag aactacatct    1560
ttggttacca cccacatggt atcatcagca tgggtagctt ctgcaccttc tccaccaacg    1620
ctactggttt cgatgacctc ttcccaggaa tcaggccttc cttgctcacc ctcaccagca    1680
acttcaacat cccactctac agggattacc tcatggcctg tggactctgc tcagtgtcta    1740
agacctcctg ccagaacatc ctcaccaagg gtggtccagg aaggtccatt gctattgtgg    1800
tgggaggtgc ctctgagtcc ttgaacgcca gaccaggagt gatggacctt gtgttgaaga    1860
ggaggtttgg attcatcaag attgctgtgc agactggtgc tagccttgtc cctaccatct    1920
cctttggtga gaatgagctt tatgagcaga ttgagagcaa tgagaactct aagcttcaca    1980
ggtggcagaa gaagatccag catgctcttg gtttcaccat gccactcttc catggaaggg    2040
gtgtgttcaa ctacgacttt ggtctcctcc cacacaggca cccaatttac accattgtgg    2100
gtaagccaat cccagtccca tctatcaagt acggtcagac caaggatgag atcatcaggg    2160
agctccatga ctcttacatg cacgctgtgc aggacctcta tgacaggtac aaggacatct    2220
acgccaagga cagggtcaag gagcttgagt ttgtggagtg aacctgcagg ggatccggta    2280
ccggatcctc tagctagagc tttcgttcgt atcatcggtt tcgacaacgt tcgtcaagtt    2340
caatgcatca gtttcattgc gcacacacca gaatcctact gagtttgagt attatggcat    2400
tgggaaaact gttttccttg taccatttgt tgtgcttgta atttactgtg ttttttattc    2460
ggttttcgct atcgaactgt gaaatggaaa tggatggaga agagttaatg aatgatatgg    2520
tccttttgtt cattctcaaa ttaatattat ttgttttttc tcttatttgt tgtgtgttga    2580
atttgaaatt ataagagata tgcaaacatt ttgttttgag taaaaatgtg tcaaatcgtg    2640
gcctctaatg accgaagtta atatgaggag taaaacactt gtagttgtac cattatgctt    2700
attcactagg caacaaatat attttcagac ctagaaaagc tgcaaatgtt actgaataca    2760
agtatgtcct cttgtgtttt agacatttat gaactttcct ttatgtaatt ttccagaatc    2820
cttgtcagat tctaatcatt gctttataat tatagttata ctcatggatt tgtagttgag    2880
tatgaaaata ttttttaatg cattttatga cttgccaatt gattgacaac atgcatcaat    2940
cgaccgtacc gcggccgctc gagcaggacc tgcagaagct agcttgatgg ggatcagatt    3000
gtcgtttccc gccttcagtt taaactatca gtgttt                              3036
```

<210> SEQ ID NO 6
<211> LENGTH: 5087
<212> TYPE: DNA
<213> ORGANISM: Glycine max

<400> SEQUENCE: 6

```
tcactcaacc agtcaatatg atcaatacac aagtgttatg caataaatat actaagactc      60
aatcttatat gcaatgtggt accatgtcaa tgaaaaacct cttcgagcgc ctaggagtac     120
atgacaagac agaccacaca ctagtaagtc aggtcactct cactaggtaa atcataggg      180 agactagtca ggatcacatt gttttgtgag aatgcttcaa ctatgtagga ttggcacata     240
cttaaatgaa cattcaaatc aggagtattt accccccaagg cctagactcc gaagagtcca     300
gtagggtctc tccttcctta ttcaagttca acccaaaaaa tatttaaaca catagactct     360
atctatgaac tgtacaaaac acacgacttt tcaattgttc tcaaaatagt tttatctcgt     420
tacacctcaa agtgattaaa ctcatcgggt tcccataatg gttcccatca caatactcgt     480
tgcacattaa cttgtcgccc ttaaagggtc ttacagtcat gtgattgtat ggttcgtagc     540
tcataactca atgcacacaa tatctcaata cacatgtatt tcataattca tcacatattc     600
```

```
aatttatcac ttcaacacaa tttcaatcac aatttcatga tcccaatata ataatttatc    660
atgctaatct agtaaatctt gtccaacaca aacaaattat ataaaaatgt ttctcataac    720
atgaggggta aaaccctca aacaatttca cataatcata tgaaaatcaa aggaataaaa    780
tcataggtca aaaacacaaa aacaccaata atactcaatt ttatcaatca attcgcatca    840
ggacatcaat tgactcgtca aacacaacaa tatcgtaatt aaaatcgtaa aagaagaatt    900
ctaattcaat aaatatctca aaataaatta taatttaatc atttaaggat ctctacatgg    960
atcagcaatg agtatgatgg tcaatatgga gaaaagaaaa gagtaattac caattttttt   1020
tcaattcaaa aatgtagatg tccgcagcgt tattataaaa tgaaagtaca ttttgataaa   1080
acgacaaatt acgatccgtc gtatttatag gcgaaagcaa taaacaaatt attctaattc   1140
ggaaatcttt atttcgacgt gtctacattc acgtccaaat gggggcttag atgagaaact   1200
tcacgatttg gcgcgccaaa gcttgatatc gaattcctgc agccccctta attaagggg    1260 ggatccacta gttctagagg atccccggca aaaacattta atacgtatta tttaagaaaa   1320
aaatatgtaa taatatattt atattttaat atctattctt atgtattttt taaaaatcta   1380
ttatatattg atcaactaaa atattttttat atctacactt attttgcatt tttatcaatt   1440
ttcttgcgtt ttttggcata tttaataatg actattcttt aataatcaat cattattctt   1500
acatggtaca tattgttgga accatatgaa gtgtccattg catttgacta tgtggatagt   1560
gttttgatcc aggcctccat ttgccgctta ttaattaatt tggtaacagt ccgtactaat   1620
cagttactta tccttcctcc atcataatta atcttggtag tctcgaatgc acaacactg   1680 actagtctct tggatcataa gaaaaagcca aggaacaaaa gaagacaaaa cacaatgaga   1740
gtatcctttg catagcaatg tctaagttca taaaattcaa acaaaaacgc aatcacacac   1800
agtggacatc acttatccac tagctgatca ggatcgccgc gtcaagaaaa aaaaactgga   1860
ccccaaaagc catgcacaac aacacgtact cacaaaggtg tcaatcgagc agcccaaaac   1920
attcaccaac tcaacccatc atgagcccac acatttgttg tttctaaccc aacctcaaac   1980
tcgtattctc ttccgccacc tcattttttgt ttatttcaac acccgtcaaa ctgcatgcca   2040
ccccgtggcc aaatgtccat gcatgttaac aagacctatg actataaata tctgcaatct   2100
cggcccaggt tttcatcatc aagaaccggg taccgggccg caccatggct agcaaggacc   2160
agcacctcca acagaaggtg aagcacaccc ttgaggccat cccatcccct aggtatgctc   2220
cactcagggt cccacttagg agaaggctcc aaaccctgc tgttctcctc tggtgctcca   2280
tgatgagcat ctgcatgttc atcttcttct tcctctgcag catccctgtg ctcctttggt   2340
tcccaattat cctctacttg acctggattt tggtgtggga taaggcccct gagaacggag   2400
gcagacctat caggtggctc aggaacgcag cttggtggaa gctctttgct ggatacttcc   2460
cagctcatgt tatcaaggag gctgaccttg acccatccaa gaactacatc tttggttacc   2520
acccacatgg tatcatcagc atgggtagct ctgcacctt ctccaccaac gctactggtt   2580
tcgatgacct cttcccagga atcaggcctt ccttgctcac cctcaccagc aacttcaaca   2640
tcccactcta cagggattac ctcatggcct gtggactctg gtcagtgtct aagacctcct   2700
gccagaacat cctcaccaag ggtggtccag gaaggtccag tgctattgtg gtgggaggtg   2760
cctctgagtc cttgaacgcc agaccaggag tgatggacct tgtgttgaag aggaggtttg   2820
gattcatcaa gattgctgtg cagactggtg ctagccttgt ccctaccatc tcctttggtg   2880
agaatgagct ttatgagcag attgagagca atgagaactc taagcttcac aggtggcaga   2940
```

```
agaagatcca gcatgctctt ggtttcacca tgccactctt ccatggaagg ggtgtgttca    3000
actacgactt tggtctcctc ccacacaggc acccaattta caccattgtg ggtaagccaa    3060
tcccagtccc atctatcaag tacggtcaga ccaaggatga gatcatcagg gagctccatg    3120
actcttacat gcacgctgtg caggacctct atgacaggta caaggacatc tacgccaagg    3180
acagggtcaa ggagcttgag tttgtggagt gaacctgcag gggatccggt accggatcct    3240
ctagctagag ctttcgttcg tatcatcggt tcgacaacg ttcgtcaagt tcaatgcatc    3300
agtttcattg cgcacacacc agaatcctac tgagtttgag tattatggca ttgggaaaac    3360
tgttttctt gtaccatttg ttgtgcttgt aatttactgt gttttttatt cggttttcgc    3420
tatcgaactg tgaaatggaa atggatggag aagagttaat gaatgatatg gtccttttgt    3480
tcattctcaa attaatatta tttgtttttt ctcttatttg ttgtgtgttg aatttgaaat    3540
tataagagat atgcaaacat tttgttttga gtaaaaatgt gtcaaatcgt ggcctctaat    3600
gaccgaagtt aatatgagga gtaaaacact tgtagttgta ccattatgct tattcactag    3660
gcaacaaata tattttcaga cctagaaaag ctgcaaatgt tactgaatac aagtatgtcc    3720
tcttgtgttt tagacattta tgaactttcc tttatgtaat tttccagaat ccttgtcaga    3780
ttctaatcat tgctttataa ttatagttat actcatggat ttgtagttga gtatgaaaat    3840
attttttaat gcattttatg acttgccaat tgattgacaa catgcatcaa tcgaccgtac    3900
cgcggccgct cgagcaggac ctgcagaagc tagcttgatg gggatcagat tgtcgtttcc    3960
cgccttcagt ttaaactatc agtgttttcc atcatactca ttgcgataaa atgtaaaaat    4020
ggacctaata tatctatatt tatagttaga gtacttcctt tctattattt actttatttt    4080
tttattttat tattttataa cacaaaaatt tatgttattc cctatcaaat taataaataa    4140
aacattattt ttatttttta ataacatata tttatttttat ttatcttaaa attattattt    4200
taattaataa aactatctct tcttatttat ttaattataa aattttcatt attttcttta    4260
aactttttt tattttaaa taaaatcatt tttaatttat ttcacgagaa atgaaatgtt    4320
acattatcca ctatttatcc taaacccata aaatatcata ttcactggag cttttttgct    4380
aactaaaata aaaaaatcca tcactttatt tttcaatgac cggtcccttta ataatctcta    4440
aagtaaactt acttttaat atcaaaattt gacattaaat tatatagggg aaccatttta    4500
atgtaaaata aattatatta aaagatcact ttattttcaa aaattgatct ttttttgtag    4560
gtgtaaaaaa tattctttga ttgataactt ctctgaaaaa taataaagat cactaaaaca    4620
ttactttat caataaaatt ctttttatg catatatttc tggttattc agaaactgaa    4680
atcaaaagta tcacatacta ctatatattt tttattactt tttcttgtgt acatatattt    4740
actattactg taactaaatg gttttaaagg tagataaaaa aaaactaatg atttaaaga    4800
aagagatata tatttagttt tttaattatt tgctgttgat gggtgggttg cgtatgacgt    4860
gtgattattc tatactataa taacgtttcg cttttggagg aaatgttct tgctgcgcac    4920
gggtacacgt acaattatac aaccagatca tcactctgaa gggacaaaag aaacaaaggc    4980
ataaaaaaac acataaccaa aaccagccat ttcgtagtta tgaagagttg caggaagttg    5040
aagcgttgca gatgggtgaa aacagtggac agtggctcta catcgac                 5087
```

<210> SEQ ID NO 7
<211> LENGTH: 3549
<212> TYPE: DNA
<213> ORGANISM: Glycine max

<400> SEQUENCE: 7

-continued

```
aaaagtccca tgtggatcac tccgttgccc cgtcgctcac cgtgttgggg ggaaggtgca    60
catggctcag ttctcaatgg aaattatctg cctaaccggc tcagttctgc gtagaaacca   120
acatgcaagc tccaccgggt gcaaagcggc agcggcggca ggatatattc aattgtaaat   180
ggcttcatgt ccgggaaatc tacatggatc agcaatgagt atgatggtca atatggagaa   240
aaagaaagag taattaccaa ttttttttca attcaaaaat gtagatgtcc gcagcgttat   300
tataaaatga aagtacattt tgataaaacg acaaattacg atccgtcgta tttataggcg   360
aaagcaataa acaaattatt ctaattcgga aatctttatt tcgacgtgtc tacattcacg   420
tccaaatggg ggcttagatg agaaacttca cgatttggcg cgccaaagct tgatatcgaa   480
ttcctgcagc cccttaatt aaggggggga tccactagtt ctagaggatc cccggcaaaa   540
acatttaata cgtattattt aagaaaaaaa tatgtaataa tatatttata ttttaatatc   600
tattcttatg tattttttaa aaatctatta tatattgatc aactaaaata tttttatatc   660
tacacttatt ttgcattttt atcaattttc ttgcgttttt tggcatattt aataatgact   720
attctttaat aatcaatcat tattcttaca tggtacatat tgttggaacc atatgaagtg   780
tccattgcat ttgactatgt ggatagtgtt ttgatccagg cctccatttg ccgcttatta   840
attaatttgg taacagtccg tactaatcag ttacttatcc ttcctccatc ataattaatc   900
ttggtagtct cgaatgccac aacactgact agtctcttgg atcataagaa aaagccaagg   960
aacaaaagaa gacaaaacac aatgagagta tcctttgcat agcaatgtct aagttcataa  1020
aattcaaaca aaaacgcaat cacacacagt ggacatcact tatccactag ctgatcagga  1080
tcgccgcgtc aagaaaaaaa aactggaccc caaaagccat gcacaacaac acgtactcac  1140
aaaggtgtca atcgagcagc ccaaaacatt caccaactca acccatcatg agcccacaca  1200
tttgttgttt ctaacccaac ctcaaaactcg tattctcttc cgccacctca ttttttgttta  1260
tttcaacacc cgtcaaactg catgccaccc cgtggccaaa tgtccatgca tgttaacaag  1320
acctatgact ataaatatct gcaatctcgg cccaggtttt catcatcaag aaccgggtac  1380
cgggccgcac catggctagc aaggaccagc acctccaaca gaaggtgaag cacacccttg  1440
aggccatccc atccctagg tatgctccac tcagggtccc acttaggaga aggctccaaa  1500
cccttgctgt tctcctctgg tgctccatga tgagcatctg catgttcatc ttcttcttcc  1560
tctgcagcat ccctgtgctc ctttggttcc caattatcct ctacttgacc tggattttgg  1620
tgtgggataa ggcccctgag aacggaggca gacctatcag gtggctcagg aacgcagctt  1680
ggtggaagct ctttgctgga tacttcccag ctcatgttat caaggaggct gaccttgacc  1740
catccaagaa ctacatcttt ggttaccacc cacatggtat catcagcatg ggtagcttct  1800
gcaccttctc caccaacgct actggttcg atgacctctt cccaggaatc aggccttcct  1860
tgctcaccct caccagcaac ttcaacatcc cactctacag ggattacctc atggcctgtg  1920
gactctgctc agtgtctaag acctcctgcc agaacatcct caccaagggt ggtccaggaa  1980
ggtccattgc tattgtggtg ggaggtgcct ctgagtcctt gaacgccaga ccaggagtga  2040
tggaccttgt gttgaagagg aggtttggat tcatcaagat tgctgtgcag actggtgcta  2100
gccttgtccc taccatctcc tttggtgaga atgagcttta tgagcagatt gagagcaatg  2160
agaactctaa gcttcacagg tggcagaaga agatccagca tgctcttggt ttcaccatgc  2220
cactcttcca tggaagggt gtgttcaact acgactttgg tctcctccca cacaggcacc  2280
caatttacac cattgtgggt aagccaatcc cagtcccatc tatcaagtac ggtcagacca  2340
```

```
aggatgagat catcagggag ctccatgact cttacatgca cgctgtgcag gacctctatg    2400
acaggtacaa ggacatctac gccaaggaca gggtcaagga gcttgagttt gtggagtgaa    2460
cctgcagggg atccggtacc ggatcctcta gctagagctt tcgttcgtat catcggtttc    2520
gacaacgttc gtcaagttca atgcatcagt ttcattgcgc acacaccaga atcctactga    2580
gtttgagtat tatggcattg ggaaaactgt ttttcttgta ccatttgttg tgcttgtaat    2640
ttactgtgtt ttttattcgg ttttcgctat cgaactgtga atggaaatg  gatggagaag    2700 agttaatgaa tgatatggtc cttttgttca ttctcaaatt aatattattt gttttttctc    2760
ttatttgttg tgtgttgaat ttgaaattat aagagatatg caaacatttt gttttgagta    2820
aaaatgtgtc aaatcgtggc ctctaatgac cgaagttaat atgaggagta aaacacttgt    2880
agttgtacca ttatgcttat tcactaggca acaaatatat tttcagacct agaaaagctg    2940
caaatgttac tgaatacaag tatgtcctct tgtgttttag acatttatga actttccttt    3000
atgtaatttt ccagaatcct tgtcagattc taatcattgc tttataatta tagttatact    3060
catggatttg tagttgagta tgaaaatatt ttttaatgca tttatgact  tgccaattga    3120 ttgacaacat gcatcaatcg accgtaccgc ggccgctcga gcaggacctg cagaagctag    3180
cttgatgggg atcagattgt cgtttcccgc cttcagttta aactatcagt gtttgacagg    3240
atatattggc gggtaaacct aagagaaaag agcgtttatt agaataatcg gatatttaaa    3300
agggcgtgaa aaggtttatc cgttcgtcca tttgtatgtg catgccaacc acagggttcc    3360
cctcgggagt gcttggcatt ccgtgcgata atgacttctg ttcaaccacc caaacgtcgg    3420
aaagcctgac gacggagcag cattccaaaa agatcccttg gctcgtctgg gtcggctaga    3480
aggtcgagtg ggctgctgtg gcttgatccc tcaacgcggt cgcggacgta gcgcagcgcc    3540
gaaaaatcc                                                            3549

<210> SEQ ID NO 8
<211> LENGTH: 26
<212> TYPE: DNA
<213> ORGANISM: Artificial Sequence
<220> FEATURE:
<223> OTHER INFORMATION: Primer

<400> SEQUENCE: 8
ggtccatttt tacattttat cgcaat                                           26

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
cgtttcccgc cttcagttta                                                  20

<210> SEQ ID NO 10
<211> LENGTH: 19
<212> TYPE: DNA
<213> ORGANISM: Artificial Sequence
<220> FEATURE:
<223> OTHER INFORMATION: Probe

<400> SEQUENCE: 10
tcagtgtttt ccatcatac                                                   19
```

```
<210> SEQ ID NO 11
<211> LENGTH: 35
<212> TYPE: DNA
<213> ORGANISM: Artificial Sequence
<220> FEATURE:
<223> OTHER INFORMATION: Primer

<400> SEQUENCE: 11
ctcaaaataa attataattt aatcatttaa ggatc                              35

<210> SEQ ID NO 12
<211> LENGTH: 22
<212> TYPE: DNA
<213> ORGANISM: Artificial Sequence
<220> FEATURE:
<223> OTHER INFORMATION: Probe

<400> SEQUENCE: 12
tatacatgtt cattctaact ct                                           22
```